United States Patent
Gellibolian et al.

(10) Patent No.: US 10,302,535 B2
(45) Date of Patent: May 28, 2019

(54) BIOFLUID COLLECTION AND FILTRATION DEVICE

(71) Applicant: CellectGen, LLC, Pasadena, CA (US)

(72) Inventors: Robert Gellibolian, Glendale, CA (US); Adam Markaryan, Glendale, CA (US)

(73) Assignee: CellectGen, Inc., Pasadena, CA (US)

( * ) Notice: Subject to any disclaimer, the term of this patent is extended or adjusted under 35 U.S.C. 154(b) by 256 days.

(21) Appl. No.: 15/230,460

(22) Filed: Aug. 7, 2016

(65) Prior Publication Data

US 2017/0030811 A1 Feb. 2, 2017

Related U.S. Application Data

(63) Continuation-in-part of application No. 14/484,207, filed on Sep. 11, 2014, now Pat. No. 9,816,087.
(Continued)

(51) Int. Cl.
*G01N 1/00* (2006.01)
*G01N 1/40* (2006.01)
(Continued)

(52) U.S. Cl.
CPC .......... *G01N 1/4077* (2013.01); *B01L 3/5021* (2013.01); *C12N 15/1017* (2013.01);
(Continued)

(58) Field of Classification Search
CPC .................................................. G01N 1/4077
(Continued)

(56) References Cited

U.S. PATENT DOCUMENTS 3,701,434 A * 10/1972 Moore .................... B01D 35/00
210/477
4,146,153 A * 3/1979 Bailen .................... A61J 1/2089
222/83

(Continued)

FOREIGN PATENT DOCUMENTS

WO 2015022318 A1 2/2015

OTHER PUBLICATIONS

Chiang et al., RNAPro SAL: A device for rapid and standardized collection of saliva RNA and proteins, BioTechniques 58:69-76 (Feb. 2015) doi 10.2144/000114254.
(Continued)

*Primary Examiner* — Christine T Mui
*Assistant Examiner* — Emily R. Berkeley
(74) *Attorney, Agent, or Firm* — Entralta P.C.; Justin G. Sanders; Peter D. Weinstein

(57) ABSTRACT

A filtration device is disclosed for filtering debris from a biofluid sample. In at least one embodiment, the filtration device provides a collection container having a collection chamber defined by a flexible wall, a mouth fluidly communicating with the collection chamber and formed through the collection container at a top end, and a filter device defining a bottom to the collection chamber. A quantitative container has a quantitative chamber in fluid communication with the filter device with the filter device separating the collection chamber from the quantitative chamber. A biofluid sample is introduced into the collection chamber through the mouth, and when the mouth with a collection chamber cap, the flexible wall of the collection container is squeezed to reduce the volume of the collection chamber and force the biofluid sample through the filter device, the filtered biofluid sample thereafter being contained within the quantitative chamber.

17 Claims, 16 Drawing Sheets

Related U.S. Application Data

(60) Provisional application No. 61/982,322, filed on Apr. 21, 2014, provisional application No. 61/876,778, filed on Sep. 12, 2013.

(51) Int. Cl.
*G01N 1/10* (2006.01)
*C12N 15/10* (2006.01)
*B01L 3/00* (2006.01)
*B01L 3/02* (2006.01)

(52) U.S. Cl.
CPC .............. *G01N 1/10* (2013.01); *B01L 3/0272* (2013.01); *B01L 2300/0681* (2013.01); *B01L 2400/0478* (2013.01); *G01N 2001/4088* (2013.01)

(58) Field of Classification Search
USPC ......................................................... 436/177
See application file for complete search history.

(56) References Cited

U.S. PATENT DOCUMENTS

| | | | |
|---|---|---|---|
| 4,317,455 A * | 3/1982 | Akhavi | A61B 5/150305 600/578 |
| 4,741,346 A * | 5/1988 | Wong | A61B 10/0051 422/401 |
| 4,961,432 A | 10/1990 | Guirguis | |
| 5,601,711 A | 2/1997 | Sklar et al. | |
| 6,296,764 B1 | 10/2001 | Guirguis et al. | |
| 7,176,034 B2 * | 2/2007 | Efthimiadis | A61B 10/0051 422/534 |
| 2001/0042724 A1 | 11/2001 | Sheikh-Ali | |
| 2004/0232075 A1 | 11/2004 | Wells | |
| 2008/0113357 A1 | 5/2008 | Baggio et al. | |
| 2010/0093551 A1 | 4/2010 | Montagu | |
| 2010/0102002 A1 | 4/2010 | O'Brien et al. | |

OTHER PUBLICATIONS

Choi et al., Real-time measurement of human salivary cortisol for the assessment of psychological stress using a smartphone, Sensing and Bio-Sensing Research 2 (2014) 8-11.

International Search Report PCT/US2014/055277, dated Dec. 16, 2014.

POREX® Diagnostic Materials and Filters, 2011 Porex Corporation, 2 pages.

Ruhl et al., Integrity of Proteins in Human Saliva after Sterilization by Gamma Irradiation, Applied and Environmental Microbiology, Feb. 2011, p. 749-755 vol. 77, No. 3 doi:10.1128/AEM.01374-10 Downloaded from http://aem.asm.org/.

Thanakun et al., An effective technique for the processing of saliva for the analysis of leptin and adiponectin, Peptides 47 (2013) 60-65.

* cited by examiner

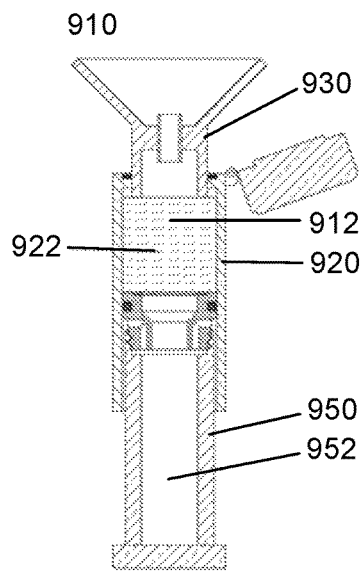
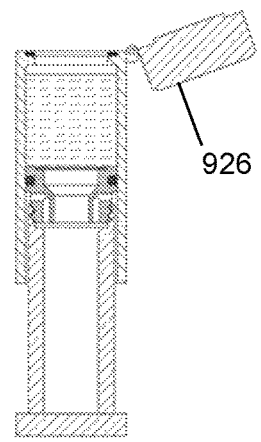
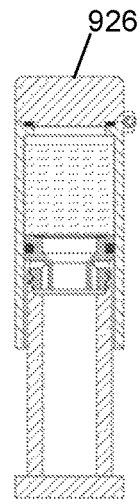
FIG. 9A     FIG. 9B     FIG. 9C
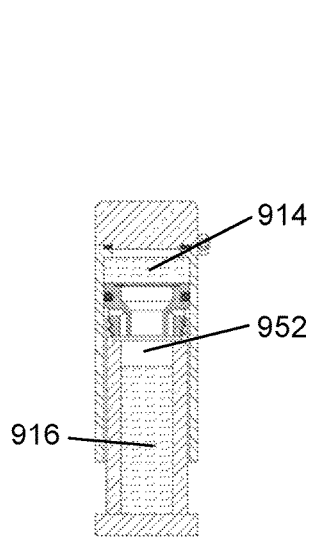
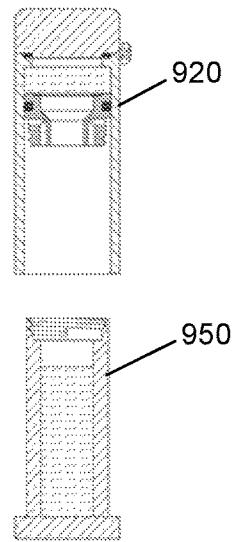
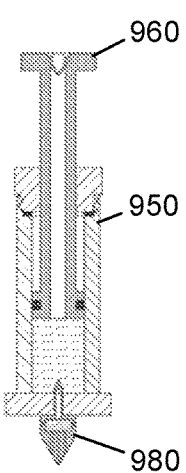
FIG. 9D     FIG. 9E     FIG. 9F

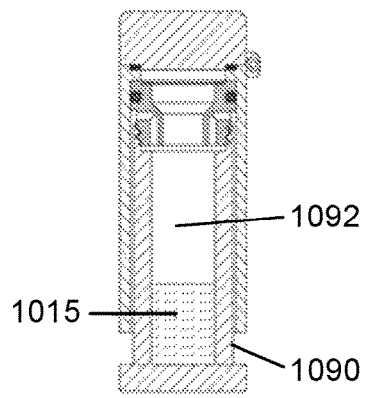
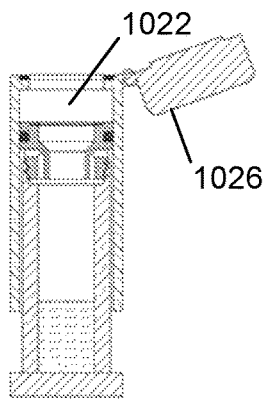
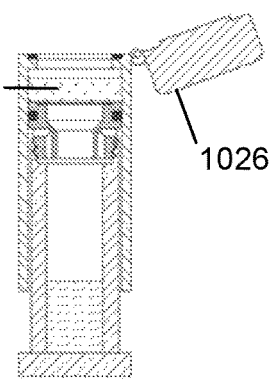
FIG. 10G     FIG. 10H     FIG. 10I
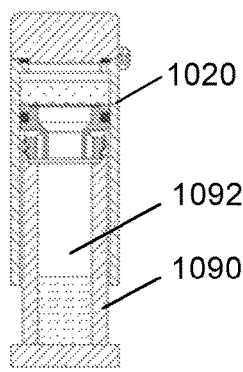
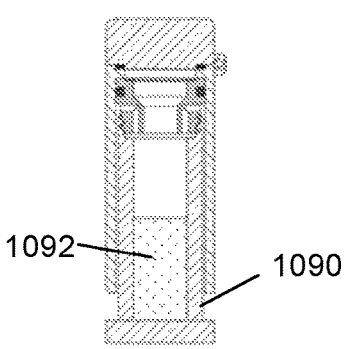
FIG. 10J     FIG. 10K

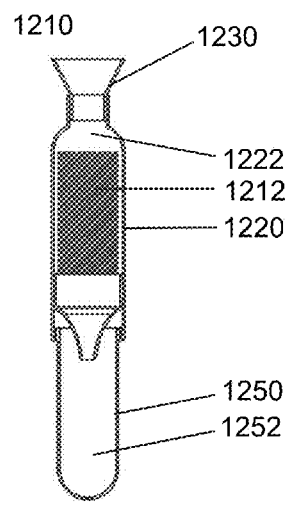
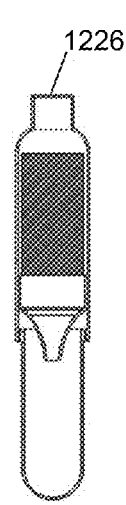
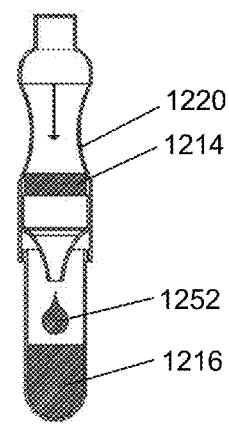
FIG. 12A  FIG. 12B  FIG. 12C
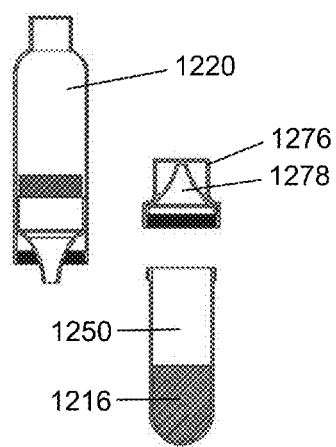
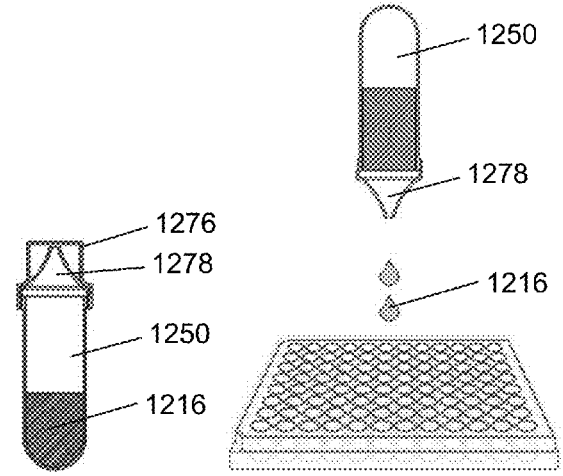
FIG. 12D  FIG. 12E  FIG. 12F

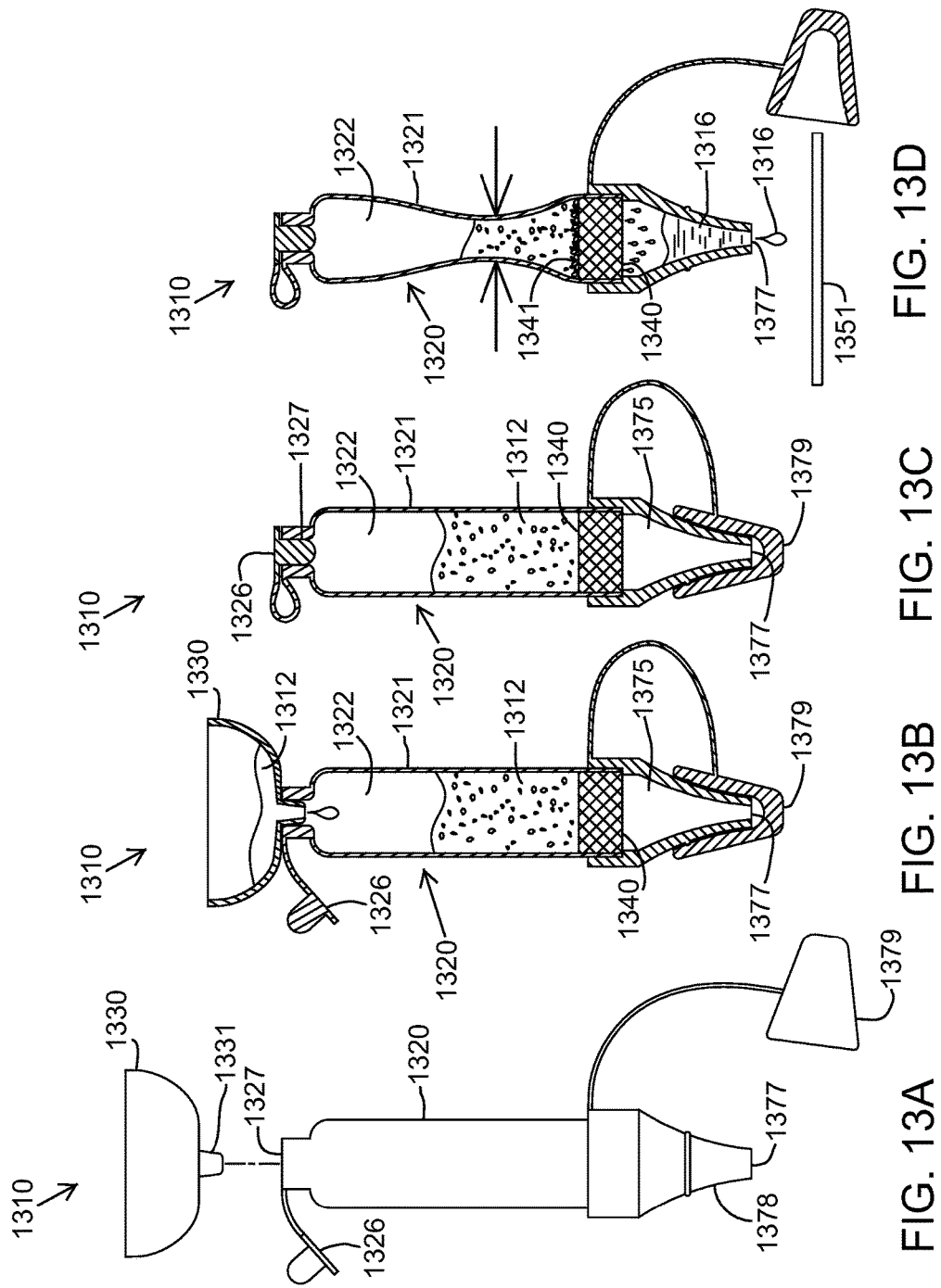

BIOFLUID COLLECTION AND FILTRATION DEVICE

INTRODUCTION

This application is a continuation-in-part of U.S. application Ser. No. 14/484,207 filed on Sep. 11, 2014, which, in turn, claims priority and is entitled to the filing date U.S. Provisional Application Ser. No. 61/982,322, filed on Apr. 21, 2014 and U.S. Provisional Application Ser. No. 61/876,778, filed on Sep. 12, 2013, the contents of each of which are hereby incorporated by reference in its entirety.

Medical and other laboratories routinely process and handle various biofluid samples in order to conduct a wide range of assays. For example, immune-based assays can detect the presence or confirm the absence of a specific antigen, antibody, or both. Similarly, polynucleotide-based assays can detect the presence or confirm the absence of a specific genetic variant, or can measure the expression levels of specific genes. As another example, activity-based assays can be performed in order to measure whether a specific molecule is functioning normally or not.

Although of great benefit, a biofluid sample typically cannot be assayed directly, in its crude form, and often must be processed in some manner before meaningful analysis can take place. Many systems, devices, and methods have been developed for the collection and purification of biofluid samples. However, these systems, devices, and methods are associated with leakage which increases risk of contaminating the collected sample as well increasing the risk of a user suffering adverse health event upon exposure to leaked biofluid sample. Other potential problems encountered include cumulative variability introduced during the multiple sample transfer steps, loss or dilution of sample through sample clinging or evaporation, introduction of contaminants, and/or sample misidentification. Lastly, these systems, devices, and methods are not standardized for quantitative collection and cannot separate and isolate human cells from non-human components of a biofluid sample, such as, e.g., viruses and bacteria.

The present specification discloses devices, methods and systems that overcome the problems identified above. As disclosed herein, the device is self-contained and multi-functional which allows for the processing of a biofluid sample without the need of multiple sample transfer steps. In addition, the devices, methods and systems disclosed herein can isolate human cells from non-human components of a biofluid sample as well as enabling rigorous and standardized quantitative collection metrics. Furthermore, the devices, methods and systems disclosed herein allow for the direct interrogation of polynucleotides. These and other advantages will be disclosed herein.

SUMMARY

Aspects of the present specification disclose a filtration device. The filtration device disclosed herein is capable of quantitative collection, separation of human and non-human components by means of size filtration, and the isolation of genetic material (DNA and/or RNA) from each component. The disclosed filtration devices may comprise a collection container comprising a collection chamber and a quantitative container comprising a quantitative chamber, wherein the quantitative container is removably attached to the collection container and wherein the quantitative container is configured to move into the collection chamber upon the application of force. The disclosed collection container comprises a filter device that upon an application of force separates the biofluid sample into a filtered component collected in the quantitative chamber and a retained component which remains in the collection chamber. The disclosed filtration devices may also comprise a collection container comprising a quantitative container comprising a quantitative chamber and a plunger device, wherein the plunger device is removably attached to the quantitative container and wherein the plunger device is configured to move into the quantitative chamber upon the application of force. In some aspects the plunger device comprises a plunger including a channel and a valve. In other aspects the plunger device comprises a plunger, a plunger filter, and a plunger chamber. The device disclosed herein is suitable in any environment including point of care use or in a clinical or laboratory setting.

Other aspects of the present specification disclose methods of processing a biofluid sample using a filtration device disclosed herein. In some aspects, the method comprises the steps of depositing a biofluid sample into the collection chamber of the filtration device; and applying a force to the filtration device whereby the biofluid sample passes through the filter of the collection chamber, a defined volume of filtered biofluid sample is collected in the quantitative chamber, and a retained biofluid sample remains in the collection chamber. In some aspects, the method comprises the steps of depositing a biofluid sample into the collection chamber of the filtration device; applying a force to the filtration device whereby the biofluid sample passes through the filter of the collection chamber, a filtered biofluid sample is collected in the quantitative chamber, and a retained biofluid sample is present in the collection chamber; removing the quantitative sample comprising the filtered biofluid sample; attaching a plunger device comprising a plunger and a channel to the quantitative chamber; and processing the filtered biofluid sample by the addition of suitable reagents using the channel. In some aspects, the method comprises the steps of depositing a biofluid sample into the collection chamber of the filtration device; applying a force to the filtration device whereby the biofluid sample passes through the filter of the collection chamber, a filtered biofluid sample is collected in a quantitative chamber, and a retained biofluid sample is present in the collection chamber; removing the quantitative sample comprising the filtered biofluid sample; attaching a plunger device comprising a plunger and a channel to the quantitative chamber; processing the filtered biofluid sample by the addition of suitable reagents using the channel; attaching the needle device comprising a needle and porous filter to the quantitative chamber; and expelling the processes filtered biofluid sample from the quantitative chamber into a collection tube using the plunger.

In some aspects, the method comprises the steps of attaching a collection container comprising a biofluid sample to the filtration device; transferring an amount of the biofluid sample to the quantitative chamber; removing the collection container from the filtration device; and applying a force to the filtration device whereby the biofluid sample passes through the quantitative filter of the quantitative container, a defined volume of filtered biofluid sample is collected in the plunger chamber, and a retained biofluid sample remains in the quantitative chamber. In some aspects, the method comprises the steps of attaching a collection container comprising a biofluid sample to the filtration device; transferring an amount of the biofluid sample to the quantitative chamber; removing the collection container from the filtration device; applying a force to the filtration device whereby the biofluid sample is separated into two or more fractions within the quantitative chamber; and applying a force to the filtration device whereby the biofluid sample passes through the quantitative filter of the quantitative container, a filtered biofluid sample is collected in the plunger chamber, and a retained biofluid sample remains in the quantitative chamber.

Other aspects of the present specification disclose systems for processing a biofluid sample. In some aspects, the system comprises a collection container, a quantitative container comprising a quantitative chamber and base, and a plunger device including a plunger, a channel, and a valve. The system may further comprise a waste container and/or a needle device. In some aspects, the system comprises a collection container, a quantitative, a waste container, and a plunger device including a plunger, a channel and a valve, and a needle device. In some aspects, the system comprises a quantitative container including a quantitative chamber and a base including a needle; a base without needle; a plunger device including a plunger, a plunger filter, and a plunger chamber. In some aspects, the system comprises a collection container; a quantitative container including a quantitative chamber and a base including a needle; a base without needle; a plunger device including a plunger, a plunger filter, and a plunger chamber.

BRIEF DESCRIPTION OF THE DRAWINGS

FIG. 9 illustrates a cross-sectional view of an embodiment for a filtration device disclosed herein in operation with FIG. 9A illustrating filtration device comprising collection container attached to collection device and containing a biofluid sample and quantitation container; FIG. 9B illustrating removal of collection device; FIG. 9C illustrating closure of collection chamber by securement of collection chamber cap; FIG. 9D illustrating filtered biofluid sample contained within quantitative chamber after application of force; FIG. 9E illustrating removal of quantitative chamber containing filtered biofluid sample from collection container containing retained biofluid sample; FIG. 9F illustrating attachment of plunger device and needle device to quantitative container.

FIG. 10 illustrates a cross-sectional view of an embodiment for a filtration device disclosed herein in operation with FIG. 10A illustrating filtration device comprising collection container attached to collection device and containing a biofluid sample and quantitation container; FIG. 10G illustrating collection of remnant biofluid sample within waste container after application of force; FIG. 10H illustrating removal of collection chamber cap; FIG. 10I illustrating addition of reagents to collection chamber; FIG. 10J illustrating closure of collection chamber by securement of collection chamber cap; and FIG. 10K illustrating collection of reagents within waste chamber after application of force.

FIG. 11 illustrates a cross-sectional view of an embodiment for a filtration device disclosed herein in operation with FIG. 11A illustrating collection container having biofluid sample in collection chamber and collection chamber cap secured.

FIG. 12 illustrates a cross-sectional view of an embodiment for a filtration device disclosed herein in operation with FIG. 12A illustrating filtration device comprising collection container attached to collection device and containing a biofluid sample and quantitation container; FIG. 12B illustrating removal of collection device and closure of collection chamber by securement of collection chamber cap; FIG. 12C illustrating application of force by squeezing wall of collection container and passage of a filtered biofluid sample into quantitative chamber after application of force; FIG. 12D illustrating removal of quantitative chamber containing filtered biofluid sample from collection container containing retained biofluid sample; FIG. 12E illustrating attachment of quantitative chamber cap; and FIG. 12F illustrating dispensing of the biofluid sample 1216.

FIG. 13A illustrates a side view of an embodiment for a filtration device disclosed herein in operation with FIG. 13B is a cross-sectional view of the filtration device comprising a collection container attached to collection device in the collection of a biofluid sample; FIG. 13C is a cross-sectional view of the filtration device illustrating containment of a biofluid sample; FIG. 13D is a cross-sectional view of the filtration device illustrating the instillation of the filtered biofluid sample to a lateral flow device.

DESCRIPTION

Figure 1:
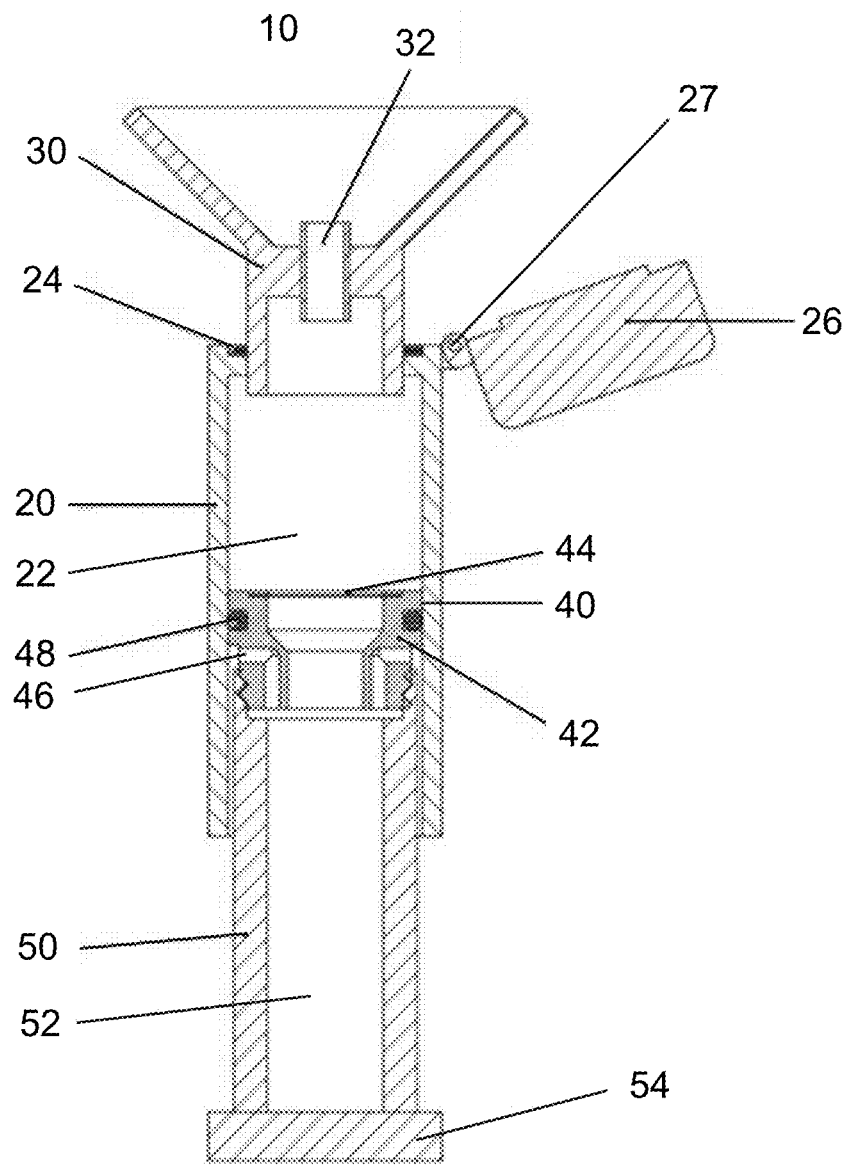
FIG. 1 illustrates a cross-sectional view of an embodiment for a filtration device disclosed herein.

Currently, two major problems are associated with the use of oral samples for diagnostic purposes. One involves the quantity and quality of polynucleotide molecules necessary to perform pharmacogenomic applications and the other involves the contaminating presents of organisms associated with an infectious disease. These two problems are very tightly interlinked in that addressing the problems associated with one exhaerbates the problems associate with the other and vice versa.

Regarding the first, pharmacogenomic applications like genotyping or sequencing require large amounts of pure polynucleotide molecules for obtaining successful and accurate results. Historically, blood samples have been used as significantly greater amount of polynucleotide molecules can be obtained relative to other biofluid samples like saliva, buccal or urine samples. For example, a blood-derived sample contains on the order of 100- to 1000-fold more amplifiable DNA, and produces a significantly higher DMET genotyping call rate, relative to the amount of amplifiable DNA obtained from a saliva-derived sample. In addition, the amount of host genomic DNA in an oral sample is only a small percentage of the total DNA due to the presence of a large amount of bacteria. For example, studies have shown that the median percentage of bacterial DNA in mouthwash samples ranges from about 50-66% of the total DNA, while the median percentage of bacterial DNA increased to 88.5% when cytobrush samples (i.e., swabbing) were used. Thus, the purity of host DNA obtained from an oral sample is greatly reduced due to the large amounts of contaminating DNA that interferes with and reduces the relative amount of host DNA.

Regarding the second, one of the key issues in diagnostic assays for infectious disease is the ability to distinguish the presence of latent viruses from active viruses. A latent virus is one where the viral DNA has integrated into the genomic DNA of the host cell and lies dormant or non-infectious. An active virus is one that is replicating and releasing viral particles outside the cell and is virulent or infectious. Typical biofluid samples are collected in a manner that fails to separate cells infected with latent viruses from active viruses. As a consequence there is a large degree of background noise due to the presence of latent viral DNA which contributes to a false positive result. Thus, there is no means of quantifying the level of infectious viral particles in assays that use biofluid samples like whole blood or saliva.

The present specification discloses a biofluid collection and filtration device and methods and kits thereof that separate host cells from other components or fractions of a biofluid sample. This allows, for example the separation of host cells from bacteria, thereby obtaining pure DNA for pharmacogenomic applications. In addition, larger amounts of host DNA can be obtained because cytobrush samples can be collected in order to obtain more host cells. In addition, the disclosed device, methods and kits enable the separation of host cells from active viral particles. This allows increased sensitivity and accuracy in assays for infectious diseases. Furthermore, the disclosed device, methods and kits allow a measured volume of a biofluid sample to be collected, filtered and processed. This improves the sensitivity and accuracy of any subsequent assay by standardizing the amount of a biofluid sample that is analyzed.

The present specification discloses a filtration device useful for purifying a crude biofluid sample including a blood sample, a urine sample or an oral sample like buccal or saliva. A filtration device disclosed herein may comprise a collection chamber, a quantitative chamber and/or a waste chamber. In operation, a crude biofluid sample is placed inside a collection chamber of the filtration device disclosed herein and a collection chamber cap is secured over the opening to provide a liquid-tight seal. Force is then applied to the filtration device causing separation of the liquids of the crude sample from the solids, such as, e.g., cells and particulate debris, using a filter located within the collection chamber. A defined volume of a cell-free liquid fraction (or filtered biofluid sample) is collected in the quantitative chamber while the retained cell sample comprising host cells remains in the collection chamber. The quantitative chamber is then removed from the collection chamber and the filtered biofluid sample may then be further processed. To assist in such processing, a plunger device may be attached to the opening of the quantitative chamber. The plunger device includes a plunger with a central channel that enables the addition of and the mixing of the reagents with the filtered biofluid sample. Typical reagents include wash solutions, cell lysis solutions, and/or buffered solutions. After processing, a needle device including a filter is attached to the quantitative chamber which enables the processes, filtered biofluid sample to be filtered once again as it is expelled from the quantitative chamber into a separate collection device.

Upon removal of the quantitative chamber, the collection chamber containing the retained cell sample may then be disposed of, or further processed. For further processing, a waste chamber may be attached to the collection chamber and an appropriate reagent, such as a wash solution, a cell lysis solution, and/or buffered solution, may then be applied to the collection chamber to further process the cells retained on the filter. Force is then applied to the filtration device causing separation of the liquid component of the reagent from the retained sample using a filter located within the collection chamber. An application of force includes manual manipulation of the filtration device by a user or mechanical manipulation of the filtration device, such as, e.g., centrifugation.

Aspects of the present specification disclose a filtration device. A filtration device disclosed herein provides for the filtration of a biofluid sample in order to separate the cellular and/or debris and/or contaminants components from the liquid portion of a biofluid sample. The cell component retained on the filter can be processed for applications such as genotyping, whereas the liquid, cell-free fraction is collected in the quantitative chamber and can be used in detection assays for infectious disease. A filtration device disclosed herein may comprise a collection container, a quantitative container, a waste container, a plunger device, a needle device, or any combination thereof. In some embodiments, the filtration device comprises a collection container and a quantitative container. In some embodiments, the filtration device comprises a collection container and a waste container. In some embodiments, the filtration device comprises a collection container, a quantitative container, and a plunger device. In some embodiments, the filtration device comprises a quantitative container, a plunger device, and a needle device.

A filtration device disclosed herein is useful to process a wide variety of biofluid samples. A wide variety of processes can take advantage of the filtration device disclosed herein, including, without limitation, purification, extraction, and/or assay processes. Non-limiting examples of processing procedures that may be conducted using the filtration device disclosed herein include separation of a sample from contaminants and/or debris, separation of a solid biofluid sample component from a liquid biofluid sample component, purification or extraction of a polypeptide fraction, such as, e.g., antibodies, enzymes, toxins, or other protein group, from a biofluid sample, purification or extraction of a polynucleotide fraction, such as, e.g., DNA or RNA, from a biofluid sample, or purification or extraction of a chemical fraction from a biofluid sample. The resulting processed biofluid sample may then be further processed, used as a read-out for an assay result, or used as a reagent useful for conducting an experimental or assay. Biofluid samples that may be processed using the filtration device disclosed herein, including, without limitation, a saliva sample, a buccal sample, a urine sample, a fecal sample, a sperm sample, a vaginal sample, or a blood sample such as, e.g., a whole blood sample, a plasma sample, or a serum sample.

The dimensions of a filtration device may be any suitable shape and size so long as the shape and size is useful for processing a biofluid sample. Typically, the shape and size of a filtration device disclosed herein will also allow for its functional placement into a centrifuge. In one embodiment, a filtration device disclosed herein is cylindrical in shape and of a size that enables placement of the filtration device in a microcentrifuge, a table-top centrifuge and/or a free-standing centrifuge. In some embodiments, a filtration device disclosed herein is cylindrical in shape and has a diameter of about 4 mm to about 15 mm and a length of about 5 mm to about 50 mm. In aspects of this embodiment, a filtration device disclosed herein is cylindrical in shape and has a diameter of, e.g., about 4 mm to about 6 mm, about 4 mm to about 8 mm, about 4 mm to about 10 mm, about 5 mm to about 7 mm, about 5 mm to about 8 mm, about 5 mm to about 10 mm, about 6 mm to about 8 mm, about 6 mm to about 9 mm, about 6 mm to about 10 mm, about 7 mm to about 8 mm, about 7 mm to about 9 mm, about 7 mm to about 10 mm, or about 8 mm to about 10 mm, and a length of, e.g., about 5 mm to about 10 mm, about 6 mm to about 10 mm, about 6 mm to about 12 mm, about 8 mm to about 12 mm, about 8 mm to about 15 mm, about 10 mm to about 15 mm, about 10 mm to about 20 mm, about 10 mm to about 25 mm, about 10 mm to about 30 mm, about 15 mm to about 20 mm, about 15 mm to about 25 mm, about 15 mm to about 30 mm, about 20 mm to about 25 mm, about 20 mm to about 30 mm, about 20 mm to about 35 mm, about 20 mm to about 40 mm, about 30 mm to about 40 mm, about 30 mm to about 45 mm, or about 30 mm to about 50 mm.

In other embodiments, a filtration device disclosed herein is cylindrical in shape and has a diameter of about 10 mm to about 20 mm and a length of about 50 mm to about 100 mm. In aspects of this embodiment, a filtration device disclosed herein is cylindrical in shape and has a diameter of, e.g., about 10 mm to about 12 mm, about 10 mm to about 15 mm, about 10 mm to about 17 mm, about 12 mm to about 15 mm, about 12 mm to about 17 mm, about 12 mm to about 20 mm, about 15 mm to about 18 mm, or about 15 mm to about 20 mm, and a length of, e.g., about 50 mm to about 60 mm, about 50 mm to about 70 mm, about 50 mm to about 80 mm, about 60 mm to about 70 mm, about 60 mm to about 80 mm, about 60 mm to about 90 mm, about 70 mm to about 80 mm, about 70 mm to about 90 mm, about 70 mm to about 100 mm, about 80 mm to about 90 mm, about 80 mm to about 100 mm, or about 90 mm to about 100 mm.

In other embodiments, a filtration device disclosed herein is cylindrical in shape and has a diameter of about 20 mm to about 40 mm and a length of about 80 mm to about 150 mm. In aspects of this embodiment, a filtration device disclosed herein is cylindrical in shape and has a diameter of, e.g., about 20 mm to about 25 mm, about 20 mm to about 30 mm, about 20 mm to about 35 mm, about 25 mm to about 30 mm, about 25 mm to about 35 mm, about 25 mm to about 40 mm, about 30 mm to about 35 mm, about 30 mm to about 40 mm, or about 35 mm to about 40 mm, and a length of, e.g., about 80 mm to about 90 mm, about 80 mm to about 100 mm, about 80 mm to about 110 mm, about 90 mm to about 100 mm, about 90 mm to about 110 mm, about 90 mm to about 120 mm, about 100 mm to about 110 mm, about 100 mm to about 120 mm, about 100 mm to about 130 mm, about 110 mm to about 120 mm, about 110 mm to about 130 mm, about 110 mm to about 140 mm, about 120 mm to about 130 mm, about 120 mm to about 140 mm, or about 120 mm to about 150 mm.

A filtration device disclosed herein may comprise, in part, a collection container. A collection container disclosed herein comprises a collection chamber for deposit of unprocessed biofluid sample. In some embodiments, a collection container disclosed herein comprises a collection chamber, a collection chamber cap, and a cap face seal. In some embodiments, a collection container disclosed herein comprises a collection chamber, a collection chamber cap, a cap face seal and finger restraints. In some embodiments, a collection container disclosed herein comprises a collection chamber, a collection chamber cap, a cap face seal and a filter device.

The dimensions of a collection container may be any suitable shape and size so long as the shape and size is useful for holding a biofluid sample deposited into the collection chamber. Typically, the shape and size of a collection container disclosed herein will also allow for its functional placement into a centrifuge. In one embodiment, a collection container disclosed herein is cylindrical in shape and of a size that enables placement of the filtration device comprising the collection container in a microcentrifuge, a table-top centrifuge and/or a free-standing centrifuge. In some embodiments, a collection container disclosed herein is cylindrical in shape and has a diameter of about 4 mm to about 10 mm and a length of about 5 mm to about 30 mm. In aspects of this embodiment, a collection container disclosed herein is cylindrical in shape and has a diameter of, e.g., about 4 mm to about 6 mm, about 4 mm to about 8 mm, about 4 mm to about 10 mm, about 5 mm to about 7 mm, about 5 mm to about 8 mm, about 5 mm to about 10 mm, about 6 mm to about 8 mm, about 6 mm to about 9 mm, about 6 mm to about 10 mm, about 7 mm to about 8 mm, about 7 mm to about 9 mm, about 7 mm to about 10 mm, or about 8 mm to about 10 mm, and a length of, e.g., about 5 mm to about 10 mm, about 6 mm to about 10 mm, about 6 mm to about 12 mm, about 8 mm to about 12 mm, about 8 mm to about 15 mm, about 10 mm to about 15 mm, about 10 mm to about 20 mm, about 10 mm to about 25 mm, about 15 mm to about 20 mm, about 15 mm to about 25 mm, about 15 mm to about 30 mm, about 20 mm to about 25 mm, or about 20 mm to about 30 mm.

In other embodiments, a collection container disclosed herein is cylindrical in shape and has a diameter of about 10 mm to about 20 mm and a length of about 50 mm to about 80 mm. In aspects of this embodiment, a collection container disclosed herein is cylindrical in shape and has a diameter of, e.g., about 10 mm to about 12 mm, about 10 mm to about 15 mm, about 10 mm to about 17 mm, about 12 mm to about 15 mm, about 12 mm to about 17 mm, about 12 mm to about 20 mm, about 15 mm to about 18 mm, or about 15 mm to about 20 mm, and a length of, e.g., about 50 mm to about 60 mm, about 50 mm to about 65 mm, about 50 mm to about 70 mm, about 60 mm to about 70 mm, about 60 mm to about 75 mm, about 60 mm to about 80 mm, or about 70 mm to about 80 mm.

In other embodiments, a collection container disclosed herein is cylindrical in shape and has a diameter of about 20 mm to about 40 mm and a length of about 80 mm to about 120 mm. In aspects of this embodiment, a collection container disclosed herein is cylindrical in shape and has a diameter of, e.g., about 20 mm to about 25 mm, about 20 mm to about 30 mm, about 20 mm to about 35 mm, about 25 mm to about 30 mm, about 25 mm to about 35 mm, about 25 mm to about 40 mm, about 30 mm to about 35 mm, about 30 mm to about 40 mm, or about 35 mm to about 40 mm, and a length of, e.g., about 80 mm to about 90 mm, about 80 mm to about 100 mm, about 80 mm to about 110 mm, about 90 mm to about 100 mm, about 90 mm to about 110 mm, about 90 mm to about 120 mm, about 100 mm to about 110 mm, about 100 mm to about 120 mm, or about 110 mm to about 120 mm.

In other embodiments, a collection container disclosed herein designed to comprise rigid walls. In this design, external force is applied in a manner that moves a quantitation chamber into a collection chamber of a collection container. The resulting pressure developed inside a collection chamber forces a biofluid sample through a filter device disclosed herein where a filtered sample is collected in a quantitation chamber.

In other embodiments, a collection container disclosed herein designed to comprise flexible walls. In this design, external force is applied in a manner that squeezes the walls of the collection container. The resulting pressure developed inside a collection chamber forces a biofluid sample through a filter device disclosed where a filtered sample is collected in a quantitation chamber.

A collection chamber is designed to hold a biofluid sample deposited by a user. The dimensions of a collection chamber may be any suitable shape and size useful for holding a volume of biofluid sample sufficient for subsequent processing and analysis. In one embodiment, a collection chamber disclosed herein may have a defined volume capacity allowing for the consistent collection of the same amount of a biofluid sample. This defined volume capacity ensures that standardized quantitative collection metrics can be achieved. In one embodiment, a collection chamber disclosed herein may have a volume capacity of about 0.2 mL to about 10.0 mL.

In aspects of this embodiment, a collection chamber disclosed herein may have a volume capacity of, e.g., about 0.2 mL, about 0.5 mL, about 0.75 mL, about 1.0 mL, about 1.2 mL, or about 1.5 mL, about 2.0 mL, about 2.5 mL, about 3.0 mL, about 3.5 mL, about 4.0 mL, about 4.5 mL, about 5.0 mL, about 5.5 mL, about 6.0 mL, about 6.5 mL, about 7.0 mL, about 7.5 mL, about 8.0 mL, about 8.5 mL, about 9.0 mL, about 9.5 mL, or about 10.0 mL. In other aspects of this embodiment, a collection chamber disclosed herein may have a volume capacity of, e.g., at least 0.2 mL, at least 0.5 mL, at least 0.75 mL, at least 1.0 mL, at least 1.2 mL, or at least 1.5 mL, at least 2.0 mL, at least 2.5 mL, at least 3.0 mL, at least 3.5 mL, at least 4.0 mL, at least 4.5 mL, at least 5.0 mL, at least 5.5 mL, at least 6.0 mL, at least 6.5 mL, at least 7.0 mL, at least 7.5 mL, at least 8.0 mL, at least 8.5 mL, at least 9.0 mL, at least 9.5 mL, or at least 10.0 mL. In yet other aspects of this embodiment, a collection chamber disclosed herein may have a volume capacity of, e.g., at most 0.2 mL, at most 0.5 mL, at most 0.75 mL, at most 1.0 mL, at most 1.2 mL, or at most 1.5 mL, at most 2.0 mL, at most 2.5 mL, at most 3.0 mL, at most 3.5 mL, at most 4.0 mL, at most 4.5 mL, at most 5.0 mL, at most 5.5 mL, at most 6.0 mL, at most 6.5 mL, at most 7.0 mL, at most 7.5 mL, at most 8.0 mL, at most 8.5 mL, at most 9.0 mL, at most 9.5 mL, or at most 10.0 mL.

In still other aspects of this embodiment, a collection chamber disclosed herein may have a volume capacity of, e.g., about 0.2 mL to about 0.5 mL, about 0.2 mL to about 0.75 mL, about 0.2 mL to about 1.0 mL, about 0.5 mL to about 0.75 mL, about 0.5 mL to about 1.0 mL, about 0.5 mL to about 1.2 mL, about 0.5 mL to about 1.5 mL, about 0.75 mL to about 1.0 mL, about 0.75 mL to about 1.2 mL, about 0.75 mL to about 1.5 mL, about 0.75 mL to about 2.0 mL, about 1.0 mL to about 1.5 mL, about 1.0 mL to about 2.0 mL, about 1.0 mL to about 2.5 mL, about 1.5 mL to about 2.0 mL, about 1.5 mL to about 2.5 mL, about 1.5 mL to about 3.0 mL, about 2.0 mL to about 2.5 mL, about 2.0 mL to about 3.0 mL, about 2.0 mL to about 3.5 mL, about 2.5 mL to about 3.0 mL, about 2.5 mL to about 3.5 mL, about 2.5 mL to about 4.0 mL, about 3.0 mL to about 3.5 mL, about 3.0 mL to about 4.0 mL, about 3.0 mL to about 4.5 mL, about 3.0 mL to about 5.0 mL, about 4.0 mL to about 5.0 mL, about 4.0 mL to about 6.0 mL, about 5.0 mL to about 6.0 mL, about 5.0 mL to about 7.0 mL, about 6.0 mL to about 7.0 mL, about 6.0 mL to about 8.0 mL, about 7.0 mL to about 8.0 mL, about 7.0 mL to about 9.0 mL, about 8.0 mL to about 10.0 mL, or about 9.0 mL to about 10.0 mL.

A collection container disclosed herein comprises, in part, a collection chamber cap. A collection chamber cap disclosed herein provides a liquid-tight seal which prevents leakage of a biofluid sample contained within the collection chamber once the collection cap is secured to the collection container. A collection chamber cap may be secured to a collection container by any mechanism that provides a liquid-tight seal which prevents leakage of a biofluid sample contained within the collection chamber. In aspects of this embodiment, mechanisms useful for securing a collection chamber cap to the collection container includes, without limitation, a threaded screw mechanism, a pressure-lock mechanism, a snap-on mechanism, or a friction-fit mechanism. In some embodiments, a collection chamber cap is removable and enables a user to open or close the collection chamber to the outside environment. In some embodiments, a collection chamber cap is non-removable.

A collection chamber cap disclosed herein may be attached to a collection container, such as, e.g., using a hinge attachment or a ring attachment. Alternatively, a collection chamber cap disclosed herein may be unattached to a collection container, and thus completely removable from the collection container.

A collection container disclosed herein may further comprise, in part, a finger restraint. A finger restraint disclosed herein assists a user in adding or removing the collection container from, e.g., a quantitative container disclosed herein, a waste container disclosed herein, and/or a plunger device disclosed herein. In function, the finger restraint provides a mechanism of physical resistance in order for a user to achieve and/or maintain an appropriate grip on a collection container in order to remove or add another component to it. The dimensions of a finger restraint may be any suitable shape and size so long as the shape and size is useful for a user to achieve and/or maintain an appropriate grip on a collection container in order to remove or add another component to it. Non-limiting examples of a finger restraint include tabs, raised ridges, stippled or rough surface. In aspects of this embodiment, a collection container may comprise, e.g., one or more finger restraints, two or more finger restraints, three or more finger restraints, four or more finger restraints, or five or more finger restraints. In other aspects, a collection container may comprise, e.g., about one to about two finger restraints, about one to about three finger restraints, about one to about five finger restraints, about one to about 10 finger restraints, about one to about 20 finger restraints, about one to about 30 finger restraints, about one to about 40 finger restraints, about one to about 50 finger restraints, about two to about three finger restraints, about two to about five finger restraints, about two to about 10 finger restraints, about two to about 20 finger restraints, about two to about 30 finger restraints, about two to about 40 finger restraints, about two to about 50 finger restraints, about five to about 10 finger restraints, about five to about 20 finger restraints, about five to about 30 finger restraints, about five to about 40 finger restraints, about five to about 50 finger restraints, about 10 to about 20 finger restraints, about 10 to about 30 finger restraints, about 10 to about 40 finger restraints, or about 10 to about 50 finger restraints.

A filtration device disclosed herein may comprise, in part, a collection device. A collection device disclosed herein provides assistance in the collection of a crude biofluid sample and its placement into a collection chamber as disclosed herein. Placement of the sample may be accomplished simply by having the individual from which the sample is being collected directly deposit the crude biofluid sample into the collection chamber, such as, e.g., by spitting saliva, poring urine, or squeezing blood droplets into the chamber. Alternatively, a collection device may be employed to aid in the collection of a crude biofluid sample. For example, a funnel may be attached to the opening of a collection chamber disclosed herein to assist in the collection of the sample. In one aspect of this embodiment, a subject may spit into the funnel and the sputum drip into the collection chamber. In another aspect of this embodiment, a subject or user may pour a biofluid sample, such as, e.g., a urine sample or blood sample, into the funnel from a separate container and thereby fill the collection chamber with a biofluid sample. In some embodiments, a collection device comprises a strainer useful for preventing large particles or debris from entering into the collection chamber as well as a providing a physical object to press a swab or other collecting instrument in order to remove a crude biofluid sample from the collecting instrument. In an aspect of this embodiment, a cotton tip including a buccal swap can be pressed against a strainer in order to deposit buccal material into the funnel. A solution or buffer could then be used to rinse the cells into the collection chamber.

A filtration device disclosed herein may comprises, in part, a filter device. A filter device provides the mechanism used to separate one component or fraction of a biofluid sample from another component or fraction. In some embodiments, a filter device comprises a filter mount, a filter, and O-ring. In some embodiments, a filter device comprises a filter mount, a port, a filter, and O-ring. In some embodiments, a filter device comprises a filter mount, a one-way check valve, a filter, and O-ring. In some embodiments, a filter device comprises a filter mount, a port, a one-way check valve, a filter, and O-ring. A filter device disclosed herein may be incorporated into a collection container disclosed herein, a quantitative container disclosed herein, or a freely detached and separate component.

In operation, after a biofluid sample is deposited into the collection chamber and closed using the collection chamber cap, a user may apply force in a manner that enables the biofluid components or fractions of sufficient size or properties to pass through the filter and into the quantitative chamber. Alternatively, the filtration device comprising the collection container and quantitative container may have force applied by using a machine, such as, e.g., a microcentrifuge, a table-top centrifuge and/or a free-standing centrifuge.

In some embodiments, force is applied on a collection container in a manner that pushes a quantitative container disclosed herein into the collection chamber. The resulting pressure developed inside a collection chamber forces a biofluid sample through a filter device disclosed herein where a filtered sample is collected in a quantitation chamber. In other embodiments, force is applied in a manner that squeezes the walls of the collection container. The resulting pressure developed inside a collection chamber forces a biofluid sample through a filter device disclosed where a filtered sample is collected in a quantitation chamber.

A filter disclosed herein enables the separation one component or fraction of a biofluid sample from another component or fraction. For example, a filter can enable the solid components, such as, e.g., cells, debris or contaminant, to be separated from the liquid components of the biofluid sample. In aspects of this embodiment, a filter useful for separating components contained in a biofluid sample can be, e.g., a size-exclusion filter, a plasma filter, an ion-exclusion filter, a magnetic filter, or an affinity filter. In other aspects of this embodiment, a filter useful for separating components contained in a biofluid sample can have a pore size of, e.g., 0.1 µm, 0.2 µm, 0.5 µm, 1.0 µm, 2.0 µm, 5.0 µm, 10.0 µm, 20.0 µm, 30 µm, 40 µm, 50 µm, 60 µm, 70 µm, 80 µm, 90 µm, 100 µm, or more. In yet other aspects of this embodiment, a filter useful for separating components contained in a biofluid sample can have a pore size of, e.g., at least 0.2 µm, at least 0.5 µm, at least 1.0 µm, at least 2.0 µm, at least 5.0 µm, at least 10.0 µm, at least 20.0 µm, at least 30.0 µm, at least 40.0 µm, at least 50.0 µm, at least 60.0 µm, at least 70.0 µm, at least 80.0 µm, at least 90.0 µm, or at least 100.0 µm. In still other aspects of this embodiment, a filter useful for separating components contained in a biofluid sample can have a pore size of, e.g., at most 0.1 µm, at most 0.2 µm, at most 0.5 µm, at most 1.0 µm, at most 2.0 µm, at most 5.0 µm, at most 10.0 µm, at most 20.0 µm, at most 30.0 µm, at most 40.0 µm, at most 50.0 µm, at most 60.0 µm, at most 70.0 µm, at most 80.0 µm, at most 90.0 µm, or at most 100.0 µm. In other aspects of this embodiment, a filter useful for separating components contained in a biofluid sample can have a pore size between, e.g., about 0.2 µm to about 0.5 µm, about 0.2 µm to about 1.0 µm, about 0.2 µm to about 2.0 µm, about 0.2 µm to about 5.0 µm, about 0.2 µm to about 10.0 µm, about 0.2 µm to about 20.0 µm, about 0.2 µm to about 30.0 µm, about 0.2 µm to about 40.0 µm, about 0.2 µm to about 50.0 µm, about 0.5 µm to about 1.0 µm, about 0.5 µm to about 2.0 µm, about 0.5 µm to about 5.0 µm, about 0.5 µm to about 10.0 µm, about 0.5 µm to about 20.0 µm, about 0.5 µm to about 30.0 µm, about 0.5 µm to about 40.0 µm, about 0.5 µm to about 50.0 µm, about 1.0 µm to about 2.0 µm, about 1.0 µm to about 5.0 µm, about 1.0 µm to about 10.0 µm, about 1.0 µm to about 20.0 µm, about 1.0 µm to about 30.0 µm, about 1.0 µm to about 40.0 µm, about 1.0 µm to about 50.0 µm, about 2.0 µm to about 5.0 µm, about 2.0 µm to about 10.0 µm, about 2.0 µm to about 20.0 µm, about 2.0 µm to about 30.0 µm, about 2.0 µm to about 40.0 µm, about 2.0 µm to about 50.0 µm, about 5.0 µm to about 10.0 µm, about 5.0 µm to about 20.0 µm, about 5.0 µm to about 30.0 µm, about 5.0 µm to about 40.0 µm, about 5.0 µm to about 50.0 µm, about 10.0 µm to about 20.0 µm, about 10.0 µm to about 30.0 µm, about 10.0 µm to about 40.0 µm, about 10.0 µm to about 50.0 µm, about 10.0 µm to about 60.0 µm, about 10.0 µm to about 70.0 µm, about 20.0 µm to about 30.0 µm, about 20.0 µm to about 40.0 µm, about 20.0 µm to about 50.0 µm, about 20.0 µm to about 60.0 µm, about 20.0 µm to about 70.0 µm, about 20.0 µm to about 80.0 µm, about 20.0 µm to about 90.0 µm, about 20.0 µm to about 100.0 µm, about 30.0 µm to about 40.0 µm, about 30.0 µm to about 50.0 µm, about 30.0 µm to about 60.0 µm, about 30.0 µm to about 70.0 µm, about 30.0 µm to about 80.0 µm, about 30.0 µm to about 90.0 µm, about 30.0 µm to about 100.0 µm, about 40.0 µm to about 50.0 µm, about 40.0 µm to about 60.0 µm, about 40.0 µm to about 70.0 µm, about 40.0 µm to about 80.0 µm, about 40.0 µm to about 90.0 µm, about 40.0 µm to about 100.0 µm, about 50.0 µm to about 60.0 µm, about 50.0 µm to about 70.0 µm, about 50.0 µm to about 80.0 µm, about 50.0 µm to about 90.0 µm, or about 50.0 µm to about 100.0 µm.

In yet other aspects of this embodiment, a filter useful for separating components contained in a biofluid sample can be, e.g., an anion filter or a cation filter. In still other aspects of this embodiment, a filter useful for separating components contained in a biofluid sample can be, e.g., an immune-affinity filter, an ion-affinity filter, a polynucleotide-affinity filter, a polypeptide-affinity filter, or a chemical-affinity filter.

A filter mount and O-ring disclosed herein holds the filter in place within the collection container, provides a liquid tight seal between the collection chamber and the quantitative chamber, and an attachment point that enables a quantitative container or waste container disclosed herein to be secured to the collection container.

A port disclosed herein enables the release of air that would otherwise create a pressure build-up when a user applies force to the filtration device causing a quantitative container disclosed herein to be pushed up into the collection chamber. In some embodiments, a port disclosed herein is integrated into a filter mount disclosed herein. In some embodiments, a port disclosed herein is integrated into a filter disclosed herein.

A one-way check valve disclosed herein enables a filtered biological sample passed into the quantitative chamber to flow back into the collection chamber in situations where the volume of the filtered biofluid sample surpasses the capacity of the defined volume of the quantitative chamber. A one-way check valve disclosed herein ensures that only the defined volume of a filtered biofluid sample is collected in the quantitative chamber. In some embodiments, a one-way check valve disclosed herein is integrated into a filter mount disclosed herein. In some embodiments, a one-way check valve disclosed herein is integrated into a filter disclosed herein.

A filtration device disclosed herein may comprise, in part, a quantitative container. A quantitative container disclosed herein provides for the collection of the biofluid sample component or fraction that passes through the filter after application of an appropriate force. For example, a quantitative container may be used to collect a liquid component or fraction of a biofluid sample passed through the filter of the collection container. In some embodiments, a quantitative container may comprise a quantitative chamber and a quantitative chamber dispenser. In some embodiments, a quantitative container may comprise a quantitative chamber and a quantitative chamber cap. In some embodiments, a quantitative container may comprise a quantitative chamber, a quantitative chamber dispenser, and a quantitative chamber cap. In some embodiments, a quantitative container may comprise a quantitative chamber. In some embodiments, a quantitative container may comprise a quantitative chamber and a base. In some embodiments, a quantitative container may comprise a quantitative chamber and a base including a base needle.

The dimensions of a quantitative container may be any suitable shape and size so long as the shape and size is useful for collecting a biofluid sample component or fraction filtered through the filter of the collection container. Typically, the shape and size of a quantitative container disclosed herein will also allow for its functional placement into a centrifuge. In one embodiment, a quantitative container disclosed herein is cylindrical in shape and of a size that enables placement of the filtration device comprising the quantitative container in a microcentrifuge, a table-top centrifuge and/or a free-standing centrifuge. In some embodiments, a quantitative container disclosed herein is cylindrical in shape and has a diameter of about 4 mm to about 10 mm and a length of about 5 mm to about 30 mm. In aspects of this embodiment, a quantitative container disclosed herein is cylindrical in shape and has a diameter of, e.g., about 4 mm to about 6 mm, about 4 mm to about 8 mm, about 4 mm to about 10 mm, about 5 mm to about 7 mm, about 5 mm to about 8 mm, about 5 mm to about 10 mm, about 6 mm to about 8 mm, about 6 mm to about 9 mm, about 6 mm to about 10 mm, about 7 mm to about 8 mm, about 7 mm to about 9 mm, about 7 mm to about 10 mm, or about 8 mm to about 10 mm, and a length of, e.g., about 5 mm to about 10 mm, about 6 mm to about 10 mm, about 6 mm to about 12 mm, about 8 mm to about 12 mm, about 8 mm to about 15 mm, about 10 mm to about 15 mm, about 10 mm to about 20 mm, about 10 mm to about 25 mm, about 15 mm to about 20 mm, about 15 mm to about 25 mm, about 15 mm to about 30 mm, about 20 mm to about 25 mm, or about 20 mm to about 30 mm.

In other embodiments, a quantitative container disclosed herein is cylindrical in shape and has a diameter of about 10 mm to about 20 mm and a length of about 50 mm to about 80 mm. In aspects of this embodiment, a quantitative container disclosed herein is cylindrical in shape and has a diameter of, e.g., about 10 mm to about 12 mm, about 10 mm to about 15 mm, about 10 mm to about 17 mm, about 12 mm to about 15 mm, about 12 mm to about 17 mm, about 12 mm to about 20 mm, about 15 mm to about 18 mm, or about 15 mm to about 20 mm, and a length of, e.g., about 50 mm to about 60 mm, about 50 mm to about 65 mm, about 50 mm to about 70 mm, about 60 mm to about 70 mm, about 60 mm to about 75 mm, about 60 mm to about 80 mm, or about 70 mm to about 80 mm.

In other embodiments, a quantitative container disclosed herein is cylindrical in shape and has a diameter of about 20 mm to about 40 mm and a length of about 80 mm to about 120 mm. In aspects of this embodiment, a quantitative container disclosed herein is cylindrical in shape and has a diameter of, e.g., about 20 mm to about 25 mm, about 20 mm to about 30 mm, about 20 mm to about 35 mm, about 25 mm to about 30 mm, about 25 mm to about 35 mm, about 25 mm to about 40 mm, about 30 mm to about 35 mm, about 30 mm to about 40 mm, or about 35 mm to about 40 mm, and a length of, e.g., about 80 mm to about 90 mm, about 80 mm to about 100 mm, about 80 mm to about 110 mm, about 90 mm to about 100 mm, about 90 mm to about 110 mm, about 90 mm to about 120 mm, about 100 mm to about 110 mm, about 100 mm to about 120 mm, or about 110 mm to about 120 mm.

In other embodiments, a quantitative container disclosed herein is designed to comprise rigid walls. In this design, external force is applied in a manner that moves a quantitation chamber into a collection chamber of a collection container. The resulting pressure developed inside a collection chamber forces a biofluid sample through a filter device disclosed herein where a filtered sample is collected in a quantitation chamber.

In other embodiments, a quantitative container disclosed herein designed to comprise flexible walls. In this design, an external force may be applied in a manner that squeezes the walls of a quantitative container. The resulting pressure developed inside a quantitative chamber forces a filtered biofluid out of a quantitation chamber.

A quantitative chamber is designed to hold a biofluid sample component or fraction deposited after an application of force. The dimensions of a quantitative chamber may be any suitable shape and size useful for holding a volume of biofluid sample component or fraction sufficient for subsequent processing and analysis. In one embodiment, a quantitative chamber disclosed herein may have a defined volume capacity allowing for the consistent collection of the same amount of a biofluid sample. This defined volume capacity ensures that standardized quantitative collection metrics can be achieved. In one embodiment, a quantitative chamber disclosed herein may have a volume capacity of about 0.2 mL to about 10.0 mL.

In aspects of this embodiment, a quantitative chamber disclosed herein may have a volume capacity of, e.g., about 0.2 mL, about 0.5 mL, about 0.75 mL, about 1.0 mL, about 1.2 mL, or about 1.5 mL, about 2.0 mL, about 2.5 mL, about 3.0 mL, about 3.5 mL, about 4.0 mL, about 4.5 mL, about 5.0 mL, about 5.5 mL, about 6.0 mL, about 6.5 mL, about 7.0 mL, about 7.5 mL, about 8.0 mL, about 8.5 mL, about 9.0 mL, about 9.5 mL, or about 10.0 mL. In other aspects of this embodiment, a quantitative chamber disclosed herein may have a volume capacity of, e.g., at least 0.2 mL, at least 0.5 mL, at least 0.75 mL, at least 1.0 mL, at least 1.2 mL, or at least 1.5 mL, at least 2.0 mL, at least 2.5 mL, at least 3.0 mL, at least 3.5 mL, at least 4.0 mL, at least 4.5 mL, at least 5.0 mL, at least 5.5 mL, at least 6.0 mL, at least 6.5 mL, at least 7.0 mL, at least 7.5 mL, at least 8.0 mL, at least 8.5 mL, at least 9.0 mL, at least 9.5 mL, or at least 10.0 mL. In yet other aspects of this embodiment, a quantitative chamber disclosed herein may have a volume capacity of, e.g., at most 0.2 mL, at most 0.5 mL, at most 0.75 mL, at most 1.0 mL, at most 1.2 mL, or at most 1.5 mL, at most 2.0 mL, at most 2.5 mL, at most 3.0 mL, at most 3.5 mL, at most 4.0 mL, at most 4.5 mL, at most 5.0 mL, at most 5.5 mL, at most 6.0 mL, at most 6.5 mL, at most 7.0 mL, at most 7.5 mL, at most 8.0 mL, at most 8.5 mL, at most 9.0 mL, at most 9.5 mL, or at most 10.0 mL.

In still other aspects of this embodiment, a quantitative chamber disclosed herein may have a volume capacity of, e.g., about 0.2 mL to about 0.5 mL, about 0.2 mL to about 0.75 mL, about 0.2 mL to about 1.0 mL, about 0.5 mL to about 0.75 mL, about 0.5 mL to about 1.0 mL, about 0.5 mL to about 1.2 mL, about 0.5 mL to about 1.5 mL, about 0.75 mL to about 1.0 mL, about 0.75 mL to about 1.2 mL, about 0.75 mL to about 1.5 mL, about 0.75 mL to about 2.0 mL, about 1.0 mL to about 1.5 mL, about 1.0 mL to about 2.0 mL, about 1.0 mL to about 2.5 mL, about 1.5 mL to about 2.0 mL, about 1.5 mL to about 2.5 mL, about 1.5 mL to about 3.0 mL, about 2.0 mL to about 2.5 mL, about 2.0 mL to about 3.0 mL, about 2.0 mL to about 3.5 mL, about 2.5 mL to about 3.0 mL, about 2.5 mL to about 3.5 mL, about 2.5 mL to about 4.0 mL, about 3.0 mL to about 3.5 mL, about 3.0 mL to about 4.0 mL, about 3.0 mL to about 4.5 mL, about 3.0 mL to about 5.0 mL, about 4.0 mL to about 5.0 mL, about 4.0 mL to about 6.0 mL, about 5.0 mL to about 6.0 mL, about 5.0 mL to about 7.0 mL, about 6.0 mL to about 7.0 mL, about 6.0 mL to about 8.0 mL, about 7.0 mL to about 8.0 mL, about 7.0 mL to about 9.0 mL, about 8.0 mL to about 10.0 mL, or about 9.0 mL to about 10.0 mL.

A quantitative container disclosed herein is designed to be removably attached to a collection container disclosed herein which enables a user to freely attach or remove the quantitative container from the collection container. In one embodiment, the quantitative container is secured to the filter mount of the filer device. Attachment of the quantitative container to a collection container provides a liquid-tight seal which prevents leakage of a biofluid sample during processing. A quantitative container may be secured to a collection container by any mechanism that provides a liquid-tight seal which prevents leakage of a biofluid sample during processing. In aspects of this embodiment, mechanisms useful for securing a quantitative container to a collection container includes, without limitation, a threaded screw mechanism, a pressure-lock mechanism, a snap-on mechanism, or a friction-fit mechanism.

A quantitative container disclosed herein may further comprise a quantitative chamber dispenser. A quantitative chamber dispenser disclosed herein enables a filtered biofluid sample contained in a quantitative chamber to be dispensed into another container. Dispensing of a biofluid may be in a metered or quantitative manner or may be unmetered or qualitative in nature. A quantitative chamber dispenser may be secured to a quantitative container by any mechanism that provides a liquid-tight seal which prevents leakage of a biofluid sample contained within the quantitative chamber. In aspects of this embodiment, mechanisms useful for securing a quantitative chamber dispenser to the quantitative container includes, without limitation, a threaded screw mechanism, a pressure-lock mechanism, a snap-on mechanism, or a friction-fit mechanism. In some embodiments, a quantitative chamber dispenser is removable and enables a user to open or close the quantitative chamber to the outside environment. A quantitative chamber dispenser disclosed herein may be attached to a quantitative container, such as, e.g., using a hinge attachment or a ring attachment. Alternatively, a quantitative chamber dispenser disclosed herein may be unattached to a quantitative container, and thus completely removable from the quantitative container.

A quantitative container disclosed herein may further comprise a quantitative chamber cap. A quantitative chamber cap disclosed herein provides a liquid-tight seal which prevents leakage of a biofluid sample contained within the quantitative chamber. A quantitative chamber cap may be secured to a quantitative container or quantitative chamber dispenser by any mechanism that provides a liquid-tight seal which prevents leakage of a biofluid sample contained within the quantitative chamber. In aspects of this embodiment, mechanisms useful for securing a quantitative chamber cap to the quantitative container or quantitative chamber dispenser includes, without limitation, a threaded screw mechanism, a pressure-lock mechanism, a snap-on mechanism, or a friction-fit mechanism. In some embodiments, a quantitative chamber cap is removable and enables a user to open or close the quantitative chamber to the outside environment. A quantitative chamber cap disclosed herein may be attached to a quantitative container or quantitative chamber dispenser, such as, e.g., using a hinge attachment or a ring attachment. Alternatively, a quantitative chamber cap disclosed herein may be unattached to a quantitative container, and thus completely removable from the quantitative container or quantitative chamber dispenser.

A quantitative container disclosed herein may further comprise a base. A base disclosed herein provides a liquid-tight seal which prevents leakage of a biofluid sample contained within the quantitative chamber. A base disclosed herein may be unremovable or removable. A removable base may be secured to a quantitative container by any mechanism that provides a liquid-tight seal which prevents leakage of a biofluid sample contained within the quantitative chamber. In aspects of this embodiment, mechanisms useful for securing a removable base to the quantitative container includes, without limitation, a threaded screw mechanism, a pressure-lock mechanism, a snap-on mechanism, or a friction-fit mechanism. In some embodiments, a base is removable and enables a user to open or close the quantitative chamber to the outside environment. A base disclosed herein may be attached to a quantitative container, such as, e.g., using a hinge attachment or a ring attachment. Alternatively, a base disclosed herein may be unattached to a quantitative container, and thus completely removable from the quantitative container.

A base disclosed herein may further comprise a base needle. A base needle disclosed herein enables the transfer of a biofluid sample from a collection chamber disclosed herein to a quantitative chamber disclosed herein. In some embodiments, a base needle is used to pierce the collection chamber cap of the collection container in order to transfer a biofluid sample from collection chamber to the quantitative chamber. In some embodiments, a removable base comprising a base needle simply replaces a removable base currently attached to the quantitative container.

The pore size of a base needle may be any suitable diameter or size useful for transferring a biofluid sample from a collection chamber disclosed herein to a quantitative chamber disclosed herein. In aspects of this embodiment, a base needle has a pore size of, e.g., 18 gauge, 21 gauge, 24 gauge, 27 gauge, or 30 gauge. In other aspects of this embodiment, a base needle has a pore size diameter of, e.g., about 0.1 mm, about 0.2, mm, about 0.3 mm, about 0.4 mm, about 0.5 mm, about 0.6 mm, about 0.7 mm, about 0.8 mm, about 0.9 mm, about 1 mm, about 2 mm, about 3 mm, about 4 mm, about 5 mm, about 6 mm, about 7 mm, about 8 mm, about 9 mm or about 10 mm. In yet other aspects of this embodiment, a base needle has a pore size diameter of, e.g., at least 0.1 mm, at least 0.2, mm, at least 0.3 mm, at least 0.4 mm, at least 0.5 mm, at least 0.6 mm, at least 0.7 mm, at least 0.8 mm, at least 0.9 mm, at least 1 mm, at least 2 mm, at least 3 mm, at least 4 mm, at least 5 mm, at least 6 mm, at least 7 mm, at least 8 mm, at least 9 mm or at least 10 mm. In still other aspects of this embodiment, a base needle has a pore size diameter of, e.g., at most 0.1 mm, at most 0.2, mm, at most 0.3 mm, at most 0.4 mm, at most 0.5 mm, at most 0.6 mm, at most 0.7 mm, at most 0.8 mm, at most 0.9 mm, at most 1 mm, at most 2 mm, at most 3 mm, at most 4 mm, at most 5 mm, at most 6 mm, at most 7 mm, at most 8 mm, at most 9 mm or at most 10 mm.

In other aspects of this embodiment, a base needle has a pore size diameter between, e.g., about 0.1 mm to about 0.5 mm, about 0.1 mm to about 1.0 mm, about 0.1 mm to about 5.0 mm, about 0.1 mm to about 10.0 mm, about 0.2 mm to about 0.5 mm, about 0.2 mm to about 1.0 mm, about 0.2 mm to about 5.0 mm, about 0.2 mm to about 10.0 mm, about 0.3 mm to about 0.6 mm, about 0.3 mm to about 1.0 mm, about 0.3 mm to about 5.0 mm, about 0.3 mm to about 10.0 mm, about 0.4 mm to about 0.7 mm, about 0.4 mm to about 1.0 mm, about 0.4 mm to about 5.0 mm, about 0.4 mm to about 10.0 mm, about 0.5 mm to about 1.0 mm, about 0.5 mm to about 5.0 mm, about 0.5 mm to about 10.0 mm, about 1.0 mm to about 5.0 mm, about 1.0 mm to about 10.0 mm, about 2.0 mm to about 5.0 mm, about 2.0 mm to about 10.0 mm, or about 5.0 mm to about 10.0 mm.

In some embodiments, the base needle may comprises a base needle filter. A base needle filter provides the mechanism used to separate one component or fraction of a biofluid sample from another component or fraction. For example, a base needle filter can retain purification beads within the quantitative chamber while allowing solutions used in processing the biologic sample to pass through the needle. The liquid component is passed as waste while the bead-bound sample component or fraction is retained by the base needle filter in the collection chamber. In aspects of this embodiment, a base needle filter useful for separating components contained in a biofluid sample can be, e.g., a size-exclusion filter, a plasma filter, an ion-exclusion filter, a magnetic filter, or an affinity filter. In other aspects of this embodiment, a base needle filter useful for separating components contained in a biofluid sample can have a pore size of, e.g., 0.2 µm, 0.5 µm, 1.0 µm, 2.0 µm, 5.0 µm, 10.0 µm, or 20.0 µm. In yet other aspects of this embodiment, a base needle filter useful for separating components contained in a biofluid sample can have a pore size of, e.g., at least 0.2 µm, at least 0.5 µm, at least 1.0 µm, at least 2.0 µm, at least 5.0 µm, at least 10.0 µm, or at least 20.0 µm. In still other aspects of this embodiment, a base needle filter useful for separating components contained in a biofluid sample can have a pore size of, e.g., at most 0.2 µm, at most 0.5 µm, at most 1.0 µm, at most 2.0 µm, at most 5.0 µm, at most 10.0 µm, or at most 20.0 µm. In other aspects of this embodiment, a base needle filter useful for separating components contained in a biofluid sample can have a pore size between, e.g., about 0.2 µm to about 0.5 µm, about 0.2 µm to about 1.0 µm, about 0.2 µm to about 2.0 µm, about 0.2 µm to about 5.0 µm, about 0.2 µm to about 10.0 µm, about 0.2 µm to about 20.0 µm, about 0.2 µm to about 30.0 µm, about 0.2 µm to about 40.0 µm, about 0.2 µm to about 50.0 µm, about 0.5 µm to about 1.0 µm, about 0.5 µm to about 2.0 µm, about 0.5 µm to about 5.0 µm, about 0.5 µm to about 10.0 µm, about 0.5 µm to about 20.0 µm, about 0.5 µm to about 30.0 µm, about 0.5 µm to about 40.0 µm, about 0.5 µm to about 50.0 µm, about 1.0 µm to about 2.0 µm, about 1.0 µm to about 5.0 µm, about 1.0 µm to about 10.0 µm, about 1.0 µm to about 20.0 µm, about 1.0 µm to about 30.0 µm, about 1.0 µm to about 40.0 µm, about 1.0 µm to about 50.0 µm, about 2.0 µm to about 5.0 µm, about 2.0 µm to about 10.0 µm, about 2.0 µm to about 20.0 µm, about 2.0 µm to about 30.0 µm, about 2.0 µm to about 40.0 µm, about 2.0 µm to about 50.0 µm, about 5.0 µm to about 10.0 µm, about 5.0 µm to about 20.0 µm, about 5.0 µm to about 30.0 µm, about 5.0 µm to about 40.0 µm, about 5.0 µm to about 50.0 µm, about 10.0 µm to about 20.0 µm, about 10.0 µm to about 30.0 µm, about 10.0 µm to about 40.0 µm, about 10.0 µm to about 50.0 µm, about 10.0 µm to about 60.0 µm, about 10.0 µm to about 70.0 µm, about 20.0 µm to about 30.0 µm, about 20.0 µm to about 40.0 µm, about 20.0 µm to about 50.0 µm, about 20.0 µm to about 60.0 µm, about 20.0 µm to about 70.0 µm, about 20.0 µm to about 80.0 µm, about 20.0 µm to about 90.0 µm, about 20.0 µm to about 100.0 µm, about 30.0 µm to about 40.0 µm, about 30.0 µm to about 50.0 µm, about 30.0 µm to about 60.0 µm, about 30.0 µm to about 70.0 µm, about 30.0 µm to about 80.0 µm, about 30.0 µm to about 90.0 µm, about 30.0 µm to about 100.0 µm, about 40.0 µm to about 50.0 µm, about 40.0 µm to about 60.0 µm, about 40.0 µm to about 70.0 µm, about 40.0 µm to about 80.0 µm, about 40.0 µm to about 90.0 µm, about 40.0 µm to about 100.0 µm, about 50.0 µm to about 60.0 µm, about 50.0 µm to about 70.0 µm, about 50.0 µm to about 80.0 µm, about 50.0 µm to about 90.0 µm, or about 50.0 µm to about 100.0 µm.

In yet other aspects of this embodiment, a base needle filter useful for separating components contained in a biofluid sample can be, e.g., an anion filter or a cation filter. In still other aspects of this embodiment, a base needle filter useful for separating components contained in a biofluid sample can be, e.g., an immune-affinity filter, an ion-affinity filter, a polynucleotide-affinity filter, a polypeptide-affinity filter, or a chemical-affinity filter.

A quantitative container disclosed herein may further comprise a quantitative filter. A quantitative filter disclosed herein provides a mechanism used to separate one component or fraction of a biofluid sample from another component or fraction. In operation, after a biofluid sample is deposited into the collection chamber and closed using the collection chamber cap, a user may apply force on the collection chamber in a manner that transfers the biofluid components or fractions of sufficient size of properties to pass through the quantitative filter and into the quantitative chamber. Alternatively, the filtration device comprising the collection container and quantitative container may have force applied by using a machine, such as, e.g., a microcentrifuge, a table-top centrifuge and/or a free-standing centrifuge.

A quantitative filter disclosed herein enables the separation one component or fraction of a biofluid sample from another component or fraction. For example, a quantitative filter can enable the solid components, such as, e.g., cells, debris or contaminant, to be separated from the liquid components of the biofluid sample. In aspects of this embodiment, a quantitative filter useful for separating components contained in a biofluid sample can be, e.g., a size-exclusion filter, a plasma filter, an ion-exclusion filter, a magnetic filter, or an affinity filter. In other aspects of this embodiment, a quantitative filter useful for separating components contained in a biofluid sample can have a pore size of, e.g., 0.2 µm, 0.5 µm, 1.0 µm, 2.0 µm, 5.0 µm, 10.0 µm, or 20.0 µm. In yet other aspects of this embodiment, a quantitative filter useful for separating components contained in a biofluid sample can have a pore size of, e.g., at least 0.2 µm, at least 0.5 µm, at least 1.0 µm, at least 2.0 µm, at least 5.0 µm, at least 10.0 µm, or at least 20.0 µm. In still other aspects of this embodiment, a quantitative filter useful for separating components contained in a biofluid sample can have a pore size of, e.g., at most 0.2 µm, at most 0.5 µm, at most 1.0 µm, at most 2.0 µm, at most 5.0 µm, at most 10.0 µm, or at most 20.0 µm. In other aspects of this embodiment, a quantitative filter useful for separating components contained in a biofluid sample can have a pore size between, e.g., about 0.2 µm to about 0.5 µm, about 0.2 µm to about 1.0 µm, about 0.2 µm to about 2.0 µm, about 0.2 µm to about 5.0 µm, about 0.2 µm to about 10.0 µm, about 0.2 µm to about 20.0 µm, about 0.2 µm to about 30.0 µm, about 0.2 µm to about 40.0 µm, about 0.2 µm to about 50.0 µm, about 0.5 µm to about 1.0 µm, about 0.5 µm to about 2.0 µm, about 0.5 µm to about 5.0 µm, about 0.5 µm to about 10.0 µm, about 0.5 µm to about 20.0 µm, about 0.5 µm to about 30.0 µm, about 0.5 µm to about 40.0 µm, about 0.5 µm to about 50.0 µm, about 1.0 µm to about 2.0 µm, about 1.0 µm to about 5.0 µm, about 1.0 µm to about 10.0 µm, about 1.0 µm to about 20.0 µm, about 1.0 µm to about 30.0 µm, about 1.0 µm to about 40.0 µm, about 1.0 µm to about 50.0 µm, about 2.0 µm to about 5.0 µm, about 2.0 µm to about 10.0 µm, about 2.0 µm to about 20.0 µm, about 2.0 µm to about 30.0 µm, about 2.0 µm to about 40.0 µm, about 2.0 µm to about 50.0 µm, about 5.0 µm to about 10.0 µm, about 5.0 µm to about 20.0 µm, about 5.0 µm to about 30.0 µm, about 5.0 µm to about 40.0 µm, about 5.0 µm to about 50.0 µm, about 10.0 µm to about 20.0 µm, about 10.0 µm to about 30.0 µm, about 10.0 µm to about 40.0 µm, about 10.0 µm to about 50.0 µm, about 10.0 µm to about 60.0 µm, about 10.0 µm to about 70.0 µm, about 20.0 µm to about 30.0 µm, about 20.0 µm to about 40.0 µm, about 20.0 µm to about 50.0 µm, about 20.0 µm to about 60.0 µm, about 20.0 µm to about 70.0 µm, about 20.0 µm to about 80.0 µm, about 20.0 µm to about 90.0 µm, about 20.0 µm to about 100.0 µm, about 30.0 µm to about 40.0 µm, about 30.0 µm to about 50.0 µm, about 30.0 µm to about 60.0 µm, about 30.0 µm to about 70.0 µm, about 30.0 µm to about 80.0 µm, about 30.0 µm to about 90.0 µm, about 30.0 µm to about 100.0 µm, about 40.0 µm to about 50.0 µm, about 40.0 µm to about 60.0 µm, about 40.0 µm to about 70.0 µm, about 40.0 µm to about 80.0 µm, about 40.0 µm to about 90.0 µm, about 40.0 µm to about 100.0 µm, about 50.0 µm to about 60.0 µm, about 50.0 µm to about 70.0 µm, about 50.0 µm to about 80.0 µm, about 50.0 µm to about 90.0 µm, or about 50.0 µm to about 100.0 µm.

In yet other aspects of this embodiment, a quantitative filter useful for separating components contained in a biofluid sample can be, e.g., an anion filter or a cation filter. In still other aspects of this embodiment, a filter useful for separating components contained in a biofluid sample can be, e.g., an immune-affinity filter, an ion-affinity filter, a polynucleotide-affinity filter, a polypeptide-affinity filter, or a chemical-affinity filter.

A filtration device disclosed herein may comprise, in part, a plunger device. A plunger device disclosed herein enables the addition of and/or the mixing of reagents with a biofluid sample component or fraction contained in the quantitative chamber. In some embodiments, a plunger device comprises a plunger including a plunger O-ring and a plunger attachment. In some embodiments, a plunger device comprises a plunger including a plunger O-ring, a plunger filter, and a plunger attachment. In some embodiments, a plunger device comprises a plunger including a plunger O-ring, a plunger filter, a plunger chamber, and a plunger attachment. In some embodiments, a plunger device comprises a plunger including a plunger O-ring, a plunger filter, and a plunger attachment. In some embodiments, a plunger device comprises a plunger including a plunger O-ring, a plunger filter, a plunger chamber, and a plunger attachment including a plunger attachment face seal. In some embodiments, a plunger device comprises a plunger including a plunger O-ring and a plunger attachment including a plunger attachment face seal. In some embodiments, a plunger device comprises a plunger including a channel and a plunger O-ring, and a plunger attachment including a plunger attachment face seal. In some embodiments, a plunger device comprises a plunger including a channel, a valve and a plunger O-ring, and a plunger attachment including a plunger attachment face seal.

A plunger is a piston-like device that may be mechanically moved up and down the length of the quantitative chamber. The plunger O-ring of the plunger forms a liquid tight seal that prevents leakage of the biofluid sample from the quantitative chamber. A plunger may further comprise a channel. A channel disclosed herein is a lumen that connects a quantitative chamber disclosed herein to the outside environment and enables a user to add a reagent into the quantitative chamber. After addition of reagent, a user can force the plunger into the quantitative chamber which allows for the mixing of the reagent with the biofluid sample. The valve, located at one end of the channel allows the release of air pressure when pulling the plunger back up from the down position.

In some embodiments, the plunger device further comprises a plunger filter. A plunger filter provides the mechanism used to separate one component or fraction of a biofluid sample from another component or fraction. For example, a plunger filter can enable the solid components, such as, e.g., cells, debris or contaminant, to be separated from the liquid components of the biofluid sample. The liquid component is passed into the plunger chamber while the solid component is retained by the plunger filter in the quantitative chamber. In aspects of this embodiment, a plunger filter useful for separating components contained in a biofluid sample can be, e.g., a size-exclusion filter, a plasma filter, an ion-exclusion filter, a magnetic filter, or an affinity filter. In other aspects of this embodiment, a plunger filter useful for separating components contained in a biofluid sample can have a pore size of, e.g., 0.2 µm, 0.5 µm, 1.0 µm, 2.0 µm, 5.0 µm, 10.0 µm, or 20.0 µm. In yet other aspects of this embodiment, a plunger filter useful for separating components contained in a biofluid sample can have a pore size of, e.g., at least 0.2 µm, at least 0.5 µm, at least 1.0 µm, at least 2.0 µm, at least 5.0 µm, at least 10.0 µm, or at least 20.0 µm. In still other aspects of this embodiment, a plunger filter useful for separating components contained in a biofluid sample can have a pore size of, e.g., at most 0.2 µm, at most 0.5 µm, at most 1.0 µm, at most 2.0 µm, at most 5.0 µm, at most 10.0 µm, or at most 20.0 µm. In other aspects of this embodiment, a plunger filter useful for separating components contained in a biofluid sample can have a pore size between, e.g., about 0.2 µm to about 0.5 µm, about 0.2 µm to about 1.0 µm, about 0.2 µm to about 2.0 µm, about 0.2 µm to about 5.0 µm, about 0.2 µm to about 10.0 µm, about 0.2 µm to about 20.0 µm, about 0.2 µm to about 30.0 µm, about 0.2 µm to about 40.0 µm, about 0.2 µm to about 50.0 µm, about 0.5 µm to about 1.0 µm, about 0.5 µm to about 2.0 µm, about 0.5 µm to about 5.0 µm, about 0.5 µm to about 10.0 µm, about 0.5 µm to about 20.0 µm, about 0.5 µm to about 30.0 µm, about 0.5 µm to about 40.0 µm, about 0.5 µm to about 50.0 µm, about 1.0 µm to about 2.0 µm, about 1.0 µm to about 5.0 µm, about 1.0 µm to about 10.0 µm, about 1.0 µm to about 20.0 µm, about 1.0 µm to about 30.0 µm, about 1.0 µm to about 40.0 µm, about 1.0 µm to about 50.0 µm, about 2.0 µm to about 5.0 µm, about 2.0 µm to about 10.0 µm, about 2.0 µm to about 20.0 µm, about 2.0 µm to about 30.0 µm, about 2.0 µm to about 40.0 µm, about 2.0 µm to about 50.0 µm, about 5.0 µm to about 10.0 µm, about 5.0 µm to about 20.0 µm, about 5.0 µm to about 30.0 µm, about 5.0 µm to about 40.0 µm, about 5.0 µm to about 50.0 µm, about 10.0 µm to about 20.0 µm, about 10.0 µm to about 30.0 µm, about 10.0 µm to about 40.0 µm, about 10.0 µm to about 50.0 µm, about 10.0 µm to about 60.0 µm, about 10.0 µm to about 70.0 µm, about 20.0 µm to about 30.0 µm, about 20.0 µm to about 40.0 µm, about 20.0 µm to about 50.0 µm, about 20.0 µm to about 60.0 µm, about 20.0 µm to about 70.0 µm, about 20.0 µm to about 80.0 µm, about 20.0 µm to about 90.0 µm, about 20.0 µm to about 100.0 µm, about 30.0 µm to about 40.0 µm, about 30.0 µm to about 50.0 µm, about 30.0 µm to about 60.0 µm, about 30.0 µm to about 70.0 µm, about 30.0 µm to about 80.0 µm, about 30.0 µm to about 90.0 µm, about 30.0 µm to about 100.0 µm, about 40.0 µm to about 50.0 µm, about 40.0 µm to about 60.0 µm, about 40.0 µm to about 70.0 µm, about 40.0 µm to about 80.0 µm, about 40.0 µm to about 90.0 µm, about 40.0 µm to about 100.0 µm, about 50.0 µm to about 60.0 µm, about 50.0 µm to about 70.0 µm, about 50.0 µm to about 80.0 µm, about 50.0 µm to about 90.0 µm, or about 50.0 µm to about 100.0 µm.

In yet other aspects of this embodiment, a plunger filter useful for separating components contained in a biofluid sample can be, e.g., an anion filter or a cation filter. In still other aspects of this embodiment, a plunger filter useful for separating components contained in a biofluid sample can be, e.g., an immune-affinity filter, an ion-affinity filter, a polynucleotide-affinity filter, a polypeptide-affinity filter, or a chemical-affinity filter.

A plunger device further comprises a plunger chamber. A plunger chamber disclosed herein provides for the collection of a biofluid sample component or fraction that passes through the plunger filter after application of an appropriate force. For example, a plunger chamber may be used to collect a liquid component or fraction of a biofluid sample passed through the plunger filter of the quantitative chamber. The dimensions of a plunger chamber may be any suitable shape and size useful for holding a volume of biofluid sample component or fraction sufficient for subsequent processing and analysis. In one embodiment, a plunger chamber disclosed herein may have a defined volume capacity allowing for the consistent collection of the same amount of a biofluid sample. This defined volume capacity ensures that standardized quantitative collection metrics can be achieved. In one embodiment, a plunger chamber disclosed herein may have a volume capacity of about 0.2 mL to about 10.0 mL.

In aspects of this embodiment, a plunger chamber disclosed herein may have a volume capacity of, e.g., about 0.2 mL, about 0.5 mL, about 0.75 mL, about 1.0 mL, about 1.2 mL, or about 1.5 mL, about 2.0 mL, about 2.5 mL, about 3.0 mL, about 3.5 mL, about 4.0 mL, about 4.5 mL, about 5.0 mL, about 5.5 mL, about 6.0 mL, about 6.5 mL, about 7.0 mL, about 7.5 mL, about 8.0 mL, about 8.5 mL, about 9.0 mL, about 9.5 mL, or about 10.0 mL. In other aspects of this embodiment, a plunger chamber disclosed herein may have a volume capacity of, e.g., at least 0.2 mL, at least 0.5 mL, at least 0.75 mL, at least 1.0 mL, at least 1.2 mL, or at least 1.5 mL, at least 2.0 mL, at least 2.5 mL, at least 3.0 mL, at least 3.5 mL, at least 4.0 mL, at least 4.5 mL, at least 5.0 mL, at least 5.5 mL, at least 6.0 mL, at least 6.5 mL, at least 7.0 mL, at least 7.5 mL, at least 8.0 mL, at least 8.5 mL, at least 9.0 mL, at least 9.5 mL, or at least 10.0 mL. In yet other aspects of this embodiment, a plunger chamber disclosed herein may have a volume capacity of, e.g., at most 0.2 mL, at most 0.5 mL, at most 0.75 mL, at most 1.0 mL, at most 1.2 mL, or at most 1.5 mL, at most 2.0 mL, at most 2.5 mL, at most 3.0 mL, at most 3.5 mL, at most 4.0 mL, at most 4.5 mL, at most 5.0 mL, at most 5.5 mL, at most 6.0 mL, at most 6.5 mL, at most 7.0 mL, at most 7.5 mL, at most 8.0 mL, at most 8.5 mL, at most 9.0 mL, at most 9.5 mL, or at most 10.0 mL.

In still other aspects of this embodiment, a plunger chamber disclosed herein may have a volume capacity of, e.g., about 0.2 mL to about 0.5 mL, about 0.2 mL to about 0.75 mL, about 0.2 mL to about 1.0 mL, about 0.5 mL to about 0.75 mL, about 0.5 mL to about 1.0 mL, about 0.5 mL to about 1.2 mL, about 0.5 mL to about 1.5 mL, about 0.75 mL to about 1.0 mL, about 0.75 mL to about 1.2 mL, about 0.75 mL to about 1.5 mL, about 0.75 mL to about 2.0 mL, about 1.0 mL to about 1.5 mL, about 1.0 mL to about 2.0 mL, about 1.0 mL to about 2.5 mL, about 1.5 mL to about 2.0 mL, about 1.5 mL to about 2.5 mL, about 1.5 mL to about 3.0 mL, about 2.0 mL to about 2.5 mL, about 2.0 mL to about 3.0 mL, about 2.0 mL to about 3.5 mL, about 2.5 mL to about 3.0 mL, about 2.5 mL to about 3.5 mL, about 2.5 mL to about 4.0 mL, about 3.0 mL to about 3.5 mL, about 3.0 mL to about 4.0 mL, about 3.0 mL to about 4.5 mL, about 3.0 mL to about 5.0 mL, about 4.0 mL to about 5.0 mL, about 4.0 mL to about 6.0 mL, about 5.0 mL to about 6.0 mL, about 5.0 mL to about 7.0 mL, about 6.0 mL to about 7.0 mL, about 6.0 mL to about 8.0 mL, about 7.0 mL to about 8.0 mL, about 7.0 mL to about 9.0 mL, about 8.0 mL to about 10.0 mL, or about 9.0 mL to about 10.0 mL.

A plunger device disclosed herein is designed to be removably attached to a quantitation container disclosed herein via the plunger attachment which enables a user to freely attach or remove the plunger device from the quantitative container. Attachment of the plunger device to a quantitative container provides a liquid-tight seal which prevents leakage of a biofluid sample during processing. A plunger device may be secured to a quantitative container by any mechanism that provides a liquid-tight seal which prevents leakage of a biofluid sample during processing. In aspects of this embodiment, mechanisms useful for securing a plunger device to a quantitative container includes, without limitation, a threaded screw mechanism, a pressure-lock mechanism, a snap-on mechanism, or a friction-fit mechanism.

A filtration device disclosed herein may comprise, in part, a needle device. A needle device disclosed herein may be attached to a quantitative container as disclosed herein and provides a mechanism for a biofluid sample component or fraction to be removed from a quantitative chamber. In some embodiments, a needle device may be attached to the bottom of a quantitative container disclosed herein and enable some components of a biofluid sample contained within the quantitative chamber to be expelled using the plunder, while retaining other components.

A needle device disclosed herein may further comprise a needle. A needle disclosed herein enables the removal of a biofluid sample from a quantitative chamber disclosed herein. In some embodiments, a needle is used to pierce the base of the quantitative container in order to transfer a biofluid sample contained within the quantitative chamber.

The pore size of a needle may be any suitable diameter or size useful for transferring a biofluid sample from a collection chamber disclosed herein to a quantitative chamber disclosed herein. In aspects of this embodiment, a needle has a pore size of, e.g., 18 gauge, 21 gauge, 24 gauge, 27 gauge, or 30 gauge. In other aspects of this embodiment, a needle has a pore size diameter of, e.g., about 0.1 mm, about 0.2, mm, about 0.3 mm, about 0.4 mm, about 0.5 mm, about 0.6 mm, about 0.7 mm, about 0.8 mm, about 0.9 mm, about 1 mm, about 2 mm, about 3 mm, about 4 mm, about 5 mm, about 6 mm, about 7 mm, about 8 mm, about 9 mm or about 10 mm. In yet other aspects of this embodiment, a needle has a pore size diameter of, e.g., at least 0.1 mm, at least 0.2, mm, at least 0.3 mm, at least 0.4 mm, at least 0.5 mm, at least 0.6 mm, at least 0.7 mm, at least 0.8 mm, at least 0.9 mm, at least 1 mm, at least 2 mm, at least 3 mm, at least 4 mm, at least 5 mm, at least 6 mm, at least 7 mm, at least 8 mm, at least 9 mm or at least 10 mm. In still other aspects of this embodiment, a needle has a pore size diameter of, e.g., at most 0.1 mm, at most 0.2, mm, at most 0.3 mm, at most 0.4 mm, at most 0.5 mm, at most 0.6 mm, at most 0.7 mm, at most 0.8 mm, at most 0.9 mm, at most 1 mm, at most 2 mm, at most 3 mm, at most 4 mm, at most 5 mm, at most 6 mm, at most 7 mm, at most 8 mm, at most 9 mm or at most 10 mm.

In other aspects of this embodiment, a needle has a pore size diameter between, e.g., about 0.1 mm to about 0.5 mm, about 0.1 mm to about 1.0 mm, about 0.1 mm to about 5.0 mm, about 0.1 mm to about 10.0 mm, about 0.2 mm to about 0.5 mm, about 0.2 mm to about 1.0 mm, about 0.2 mm to about 5.0 mm, about 0.2 mm to about 10.0 mm, about 0.3 mm to about 0.6 mm, about 0.3 mm to about 1.0 mm, about 0.3 mm to about 5.0 mm, about 0.3 mm to about 10.0 mm, about 0.4 mm to about 0.7 mm, about 0.4 mm to about 1.0 mm, about 0.4 mm to about 5.0 mm, about 0.4 mm to about 10.0 mm, about 0.5 mm to about 1.0 mm, about 0.5 mm to about 5.0 mm, about 0.5 mm to about 10.0 mm, about 1.0 mm to about 5.0 mm, about 1.0 mm to about 10.0 mm, about 2.0 mm to about 5.0 mm, about 2.0 mm to about 10.0 mm, or about 5.0 mm to about 10.0 mm.

In some embodiments, a needle device disclosed herein further comprises a needle filter. In some embodiments, a needle filter disclosed herein in located within the needle disclosed herein. A needle filter provides the mechanism used to separate one component or fraction of a biofluid sample from another component or fraction. For example, a needle filter can enable the solid components, such as, e.g., cells, debris or contaminant, to be separated from the liquid components of the biofluid sample. The liquid component is passed into the quantitative chamber while the solid component is retained by the needle filter in the collection chamber. As another example, a needle filter enables the separation of the liquid component of a biofluid sample from solid components, such as, e.g., polynucleotide molecules like DNA and RNA. The liquid component is expelled from the quantitative chamber while the solid component is retained by the needle filter in the quantitative chamber. In aspects of this embodiment, a needle filter useful for separating components contained in a biofluid sample can be, e.g., a size-exclusion filter, a plasma filter, an ion-exclusion filter, a magnetic filter, or an affinity filter. In other aspects of this embodiment, a needle filter useful for separating components contained in a biofluid sample can have a pore size of, e.g., 0.2 µm, 0.5 µm, 1.0 µm, 2.0 µm, 5.0 µm, 10.0 µm, or 20.0 µm. In yet other aspects of this embodiment, a needle filter useful for separating components contained in a biofluid sample can have a pore size of, e.g., at least 0.2 µm, at least 0.5 µm, at least 1.0 µm, at least 2.0 µm, at least 5.0 µm, at least 10.0 µm, or at least 20.0 µm. In still other aspects of this embodiment, a needle filter useful for separating components contained in a biofluid sample can have a pore size of, e.g., at most 0.2 µm, at most 0.5 µm, at most 1.0 µm, at most 2.0 µm, at most 5.0 µm, at most 10.0 µm, or at most 20.0 µm. In other aspects of this embodiment, a needle filter useful for separating components contained in a biofluid sample can have a pore size between, e.g., about 0.2 µm to about 0.5 µm, about 0.2 µm to about 1.0 µm, about 0.2 µm to about 2.0 µm, about 0.2 µm to about 5.0 µm, about 0.2 µm to about 10.0 µm, about 0.2 µm to about 20.0 µm, about 0.2 µm to about 30.0 µm, about 0.2 µm to about 40.0 µm, about 0.2 µm to about 50.0 µm, about 0.5 µm to about 1.0 µm, about 0.5 µm to about 2.0 µm, about 0.5 µm to about 5.0 µm, about 0.5 µm to about 10.0 µm, about 0.5 µm to about 20.0 µm, about 0.5 µm to about 30.0 µm, about 0.5 µm to about 40.0 µm, about 0.5 µm to about 50.0 µm, about 1.0 µm to about 2.0 µm, about 1.0 µm to about 5.0 µm, about 1.0 µm to about 10.0 µm, about 1.0 µm to about 20.0 µm, about 1.0 µm to about 30.0 µm, about 1.0 µm to about 40.0 µm, about 1.0 µm to about 50.0 µm, about 2.0 µm to about 5.0 µm, about 2.0 µm to about 10.0 µm, about 2.0 µm to about 20.0 µm, about 2.0 µm to about 30.0 µm, about 2.0 µm to about 40.0 µm, about 2.0 µm to about 50.0 µm, about 5.0 µm to about 10.0 µm, about 5.0 µm to about 20.0 µm, about 5.0 µm to about 30.0 µm, about 5.0 µm to about 40.0 µm, about 5.0 µm to about 50.0 µm, about 10.0 µm to about 20.0 µm, about 10.0 µm to about 30.0 µm, about 10.0 µm to about 40.0 µm, about 10.0 µm to about 50.0 µm, about 10.0 µm to about 60.0 µm, about 10.0 µm to about 70.0 µm, about 20.0 µm to about 30.0 µm, about 20.0 µm to about 40.0 µm, about 20.0 µm to about 50.0 µm, about 20.0 µm to about 60.0 µm, about 20.0 µm to about 70.0 µm, about 20.0 µm to about 80.0 µm, about 20.0 µm to about 90.0 µm, about 20.0 µm to about 100.0 µm, about 30.0 µm to about 40.0 µm, about 30.0 µm to about 50.0 µm, about 30.0 µm to about 60.0 µm, about 30.0 µm to about 70.0 µm, about 30.0 µm to about 80.0 µm, about 30.0 µm to about 90.0 µm, about 30.0 µm to about 100.0 µm, about 40.0 µm to about 50.0 µm, about 40.0 µm to about 60.0 µm, about 40.0 µm to about 70.0 µm, about 40.0 µm to about 80.0 µm, about 40.0 µm to about 90.0 µm, about 40.0 µm to about 100.0 µm, about 50.0 µm to about 60.0 µm, about 50.0 µm to about 70.0 µm, about 50.0 µm to about 80.0 µm, about 50.0 µm to about 90.0 µm, or about 50.0 µm to about 100.0 µm.

In yet other aspects of this embodiment, a needle filter useful for separating components contained in a biofluid sample can be, e.g., an anion filter or a cation filter. In still other aspects of this embodiment, a needle filter useful for separating components contained in a biofluid sample can be, e.g., an immune-affinity filter, an ion-affinity filter, a polynucleotide-affinity filter, a polypeptide-affinity filter, or a chemical-affinity filter.

A filtration device disclosed herein may comprise, in part, a waste chamber. A waste chamber disclosed herein provides for the collection of reagents used to process the biofluid sample retained in the collection chamber after filtration. For example, a waste chamber may be used to collect wash solutions used to wash cells retained in the collection chamber after filtration of a crude biofluid sample.

The dimensions of a waste chamber may be any suitable shape and size so long as the shape and size is useful for collecting a biofluid sample component or fraction filtered through the filter of the collection chamber. Typically, the shape and size of a collection chamber disclosed herein will also allow for its functional placement into a centrifuge. In one embodiment, a waste chamber disclosed herein is cylindrical in shape and of a size that enables placement of the filtration device comprising the waste chamber in a microcentrifuge, a table-top centrifuge and/or a free-standing centrifuge. In some embodiments, a waste chamber disclosed herein is cylindrical in shape and has a diameter of about 4 mm to about 10 mm and a length of about 5 mm to about 30 mm. In aspects of this embodiment, a waste chamber disclosed herein is cylindrical in shape and has a diameter of, e.g., about 4 mm to about 6 mm, about 4 mm to about 8 mm, about 4 mm to about 10 mm, about 5 mm to about 7 mm, about 5 mm to about 8 mm, about 5 mm to about 10 mm, about 6 mm to about 8 mm, about 6 mm to about 9 mm, about 6 mm to about 10 mm, about 7 mm to about 8 mm, about 7 mm to about 9 mm, about 7 mm to about 10 mm, or about 8 mm to about 10 mm, and a length of, e.g., about 5 mm to about 10 mm, about 6 mm to about 10 mm, about 6 mm to about 12 mm, about 8 mm to about 12 mm, about 8 mm to about 15 mm, about 10 mm to about 15 mm, about 10 mm to about 20 mm, about 10 mm to about 25 mm, about 15 mm to about 20 mm, about 15 mm to about 25 mm, about 15 mm to about 30 mm, about 20 mm to about 25 mm, or about 20 mm to about 30 mm.

In other embodiments, a waste chamber disclosed herein is cylindrical in shape and has a diameter of about 10 mm to about 20 mm and a length of about 50 mm to about 80 mm. In aspects of this embodiment, a waste chamber disclosed herein is cylindrical in shape and has a diameter of, e.g., about 10 mm to about 12 mm, about 10 mm to about 15 mm, about 10 mm to about 17 mm, about 12 mm to about 15 mm, about 12 mm to about 17 mm, about 12 mm to about 20 mm, about 15 mm to about 18 mm, or about 15 mm to about 20 mm, and a length of, e.g., about 50 mm to about 60 mm, about 50 mm to about 65 mm, about 50 mm to about 70 mm, about 60 mm to about 70 mm, about 60 mm to about 75 mm, about 60 mm to about 80 mm, or about 70 mm to about 80 mm.

In other embodiments, a waste chamber disclosed herein is cylindrical in shape and has a diameter of about 20 mm to about 40 mm and a length of about 80 mm to about 120 mm. In aspects of this embodiment, a waste chamber disclosed herein is cylindrical in shape and has a diameter of, e.g., about 20 mm to about 25 mm, about 20 mm to about 30 mm, about 20 mm to about 35 mm, about 25 mm to about 30 mm, about 25 mm to about 35 mm, about 25 mm to about 40 mm, about 30 mm to about 35 mm, about 30 mm to about 40 mm, or about 35 mm to about 40 mm, and a length of, e.g., about 80 mm to about 90 mm, about 80 mm to about 100 mm, about 80 mm to about 110 mm, about 90 mm to about 100 mm, about 90 mm to about 110 mm, about 90 mm to about 120 mm, about 100 mm to about 110 mm, about 100 mm to about 120 mm, or about 110 mm to about 120 mm.

A waste chamber is designed to hold a biofluid sample component or fraction deposited after an application of force. The dimensions of a waste chamber may be any suitable shape and size useful for holding a volume of biofluid sample sufficient for subsequent processing and analysis. In one embodiment, a waste chamber disclosed herein may have a defined volume capacity allowing for the consistent collection of the same amount of a sample. This defined volume capacity ensures that standardized quantitative collection metrics can be achieved. In one embodiment, a waste chamber disclosed herein may have a volume capacity of about 0.2 mL to about 10.0 mL.

In aspects of this embodiment, a waste chamber disclosed herein may have a volume capacity of, e.g., about 0.2 mL, about 0.5 mL, about 0.75 mL, about 1.0 mL, about 1.2 mL, or about 1.5 mL, about 2.0 mL, about 2.5 mL, about 3.0 mL, about 3.5 mL, about 4.0 mL, about 4.5 mL, about 5.0 mL, about 5.5 mL, about 6.0 mL, about 6.5 mL, about 7.0 mL, about 7.5 mL, about 8.0 mL, about 8.5 mL, about 9.0 mL, about 9.5 mL, or about 10.0 mL. In other aspects of this embodiment, a waste chamber disclosed herein may have a volume capacity of, e.g., at least 0.2 mL, at least 0.5 mL, at least 0.75 mL, at least 1.0 mL, at least 1.2 mL, or at least 1.5 mL, at least 2.0 mL, at least 2.5 mL, at least 3.0 mL, at least 3.5 mL, at least 4.0 mL, at least 4.5 mL, at least 5.0 mL, at least 5.5 mL, at least 6.0 mL, at least 6.5 mL, at least 7.0 mL, at least 7.5 mL, at least 8.0 mL, at least 8.5 mL, at least 9.0 mL, at least 9.5 mL, or at least 10.0 mL. In yet other aspects of this embodiment, a waste chamber disclosed herein may have a volume capacity of, e.g., at most 0.2 mL, at most 0.5 mL, at most 0.75 mL, at most 1.0 mL, at most 1.2 mL, or at most 1.5 mL, at most 2.0 mL, at most 2.5 mL, at most 3.0 mL, at most 3.5 mL, at most 4.0 mL, at most 4.5 mL, at most 5.0 mL, at most 5.5 mL, at most 6.0 mL, at most 6.5 mL, at most 7.0 mL, at most 7.5 mL, at most 8.0 mL, at most 8.5 mL, at most 9.0 mL, at most 9.5 mL, or at most 10.0 mL.

In still other aspects of this embodiment, a waste chamber disclosed herein may have a volume capacity of, e.g., about 0.2 mL to about 0.5 mL, about 0.2 mL to about 0.75 mL, about 0.2 mL to about 1.0 mL, about 0.5 mL to about 0.75 mL, about 0.5 mL to about 1.0 mL, about 0.5 mL to about 1.2 mL, about 0.5 mL to about 1.5 mL, about 0.75 mL to about 1.0 mL, about 0.75 mL to about 1.2 mL, about 0.75 mL to about 1.5 mL, about 0.75 mL to about 2.0 mL, about 1.0 mL to about 1.5 mL, about 1.0 mL to about 2.0 mL, about 1.0 mL to about 2.5 mL, about 1.5 mL to about 2.0 mL, about 1.5 mL to about 2.5 mL, about 1.5 mL to about 3.0 mL, about 2.0 mL to about 2.5 mL, about 2.0 mL to about 3.0 mL, about 2.0 mL to about 3.5 mL, about 2.5 mL to about 3.0 mL, about 2.5 mL to about 3.5 mL, about 2.5 mL to about 4.0 mL, about 3.0 mL to about 3.5 mL, about 3.0 mL to about 4.0 mL, about 3.0 mL to about 4.5 mL, about 3.0 mL to about 5.0 mL, about 4.0 mL to about 5.0 mL, about 4.0 mL to about 6.0 mL, about 5.0 mL to about 6.0 mL, about 5.0 mL to about 7.0 mL, about 6.0 mL to about 7.0 mL, about 6.0 mL to about 8.0 mL, about 7.0 mL to about 8.0 mL, about 7.0 mL to about 9.0 mL, about 8.0 mL to about 10.0 mL, or about 9.0 mL to about 10.0 mL.

A waste chamber disclosed herein is designed to be removably attached to a collection chamber disclosed herein which enables a user to freely attach or remove the waste chamber from the collection chamber. In one embodiment, the waste chamber is secured to the filter mount of the collection chamber. Attachment of the waste chamber to a collection chamber provides a liquid-tight seal which prevents leakage of a biofluid sample during processing. A waste chamber may be secured to a collection chamber by any mechanism that provides a liquid-tight seal which prevents leakage of a biofluid sample during processing. In aspects of this embodiment, mechanisms useful for securing a waste chamber to a collection chamber includes, without limitation, a threaded screw mechanism, a pressure-lock mechanism, a snap-on mechanism, or a friction-fit mechanism.

Figure 2:
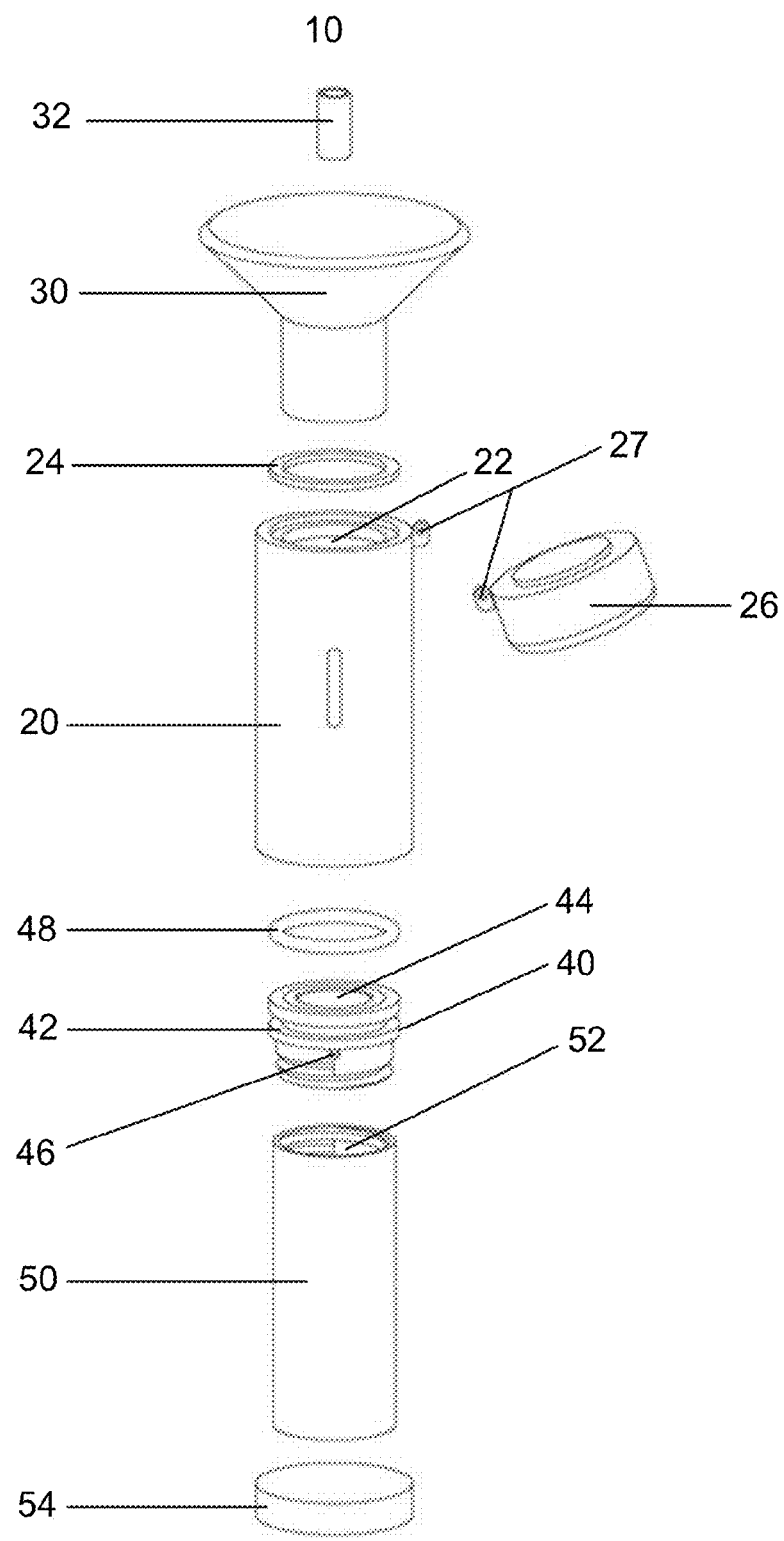
FIG. 2 illustrates a telescopic perspective view of an embodiment for a filtration device disclosed herein.

In one embodiment, filtration device 10 comprises collection container 20 and quantitative container 50 (FIG. 1). Collection container 20 comprises collection chamber 22, cap face seal 24, and filter device 40 comprising filter mount 42, filter 44, port 46, and filter mount O-ring 48 (FIG. 1). In an aspect of this embodiment, collection chamber cap 26 is attached via hinged mechanism 27 to collection container 20. FIG. 1 also illustrates the placement of collection device 30 comprising strainer 32 to collection container 20. Quantitative container 50 comprises quantitative chamber 52 and base 54 (FIG. 1). A telescopic perspective view of this embodiment is shown in FIG. 2.

Figure 3:
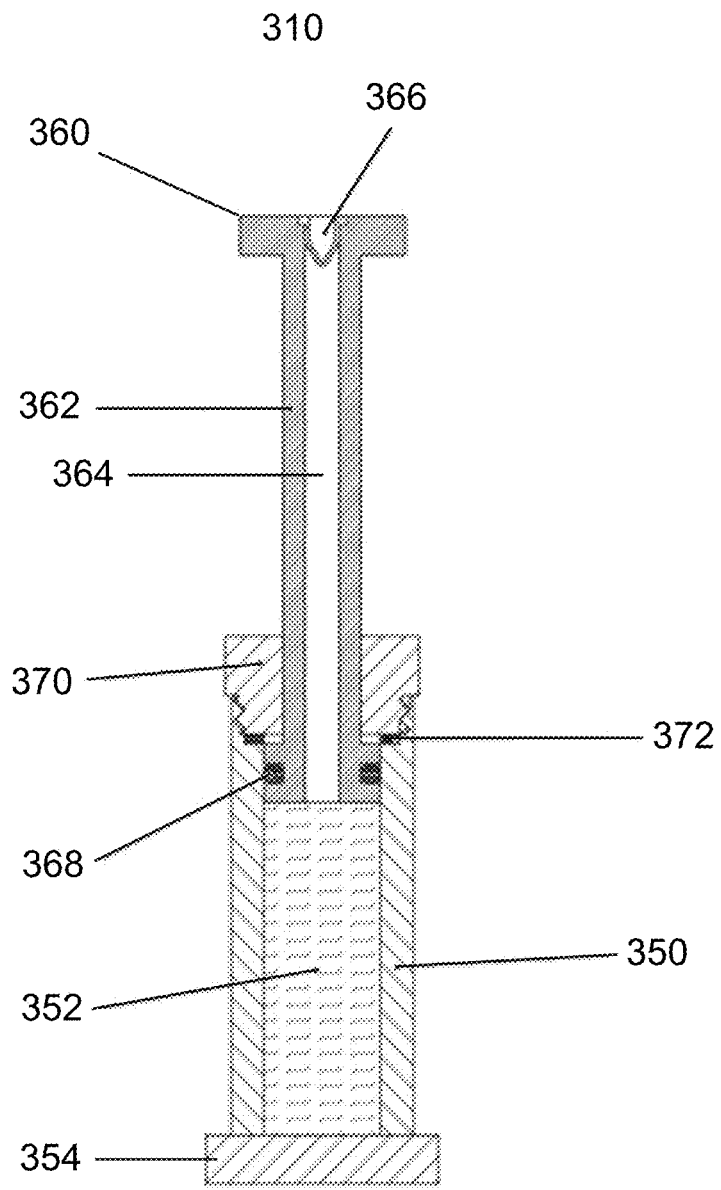
FIG. 3 illustrates a cross-sectional view of an embodiment for a filtration device disclosed herein.

In another embodiment, filtration device 310 comprises quantitative container 350 and plunger device 360 (FIG. 3). Quantitative container 350 comprises quantitative chamber 352 and base 354 (FIG. 3). Plunger device 360 comprises plunger 362, channel 364, valve 366, plunger O-ring 368, plunger attachment 370 and plunger attachment face seal 372 (FIG. 3).

Figure 4:
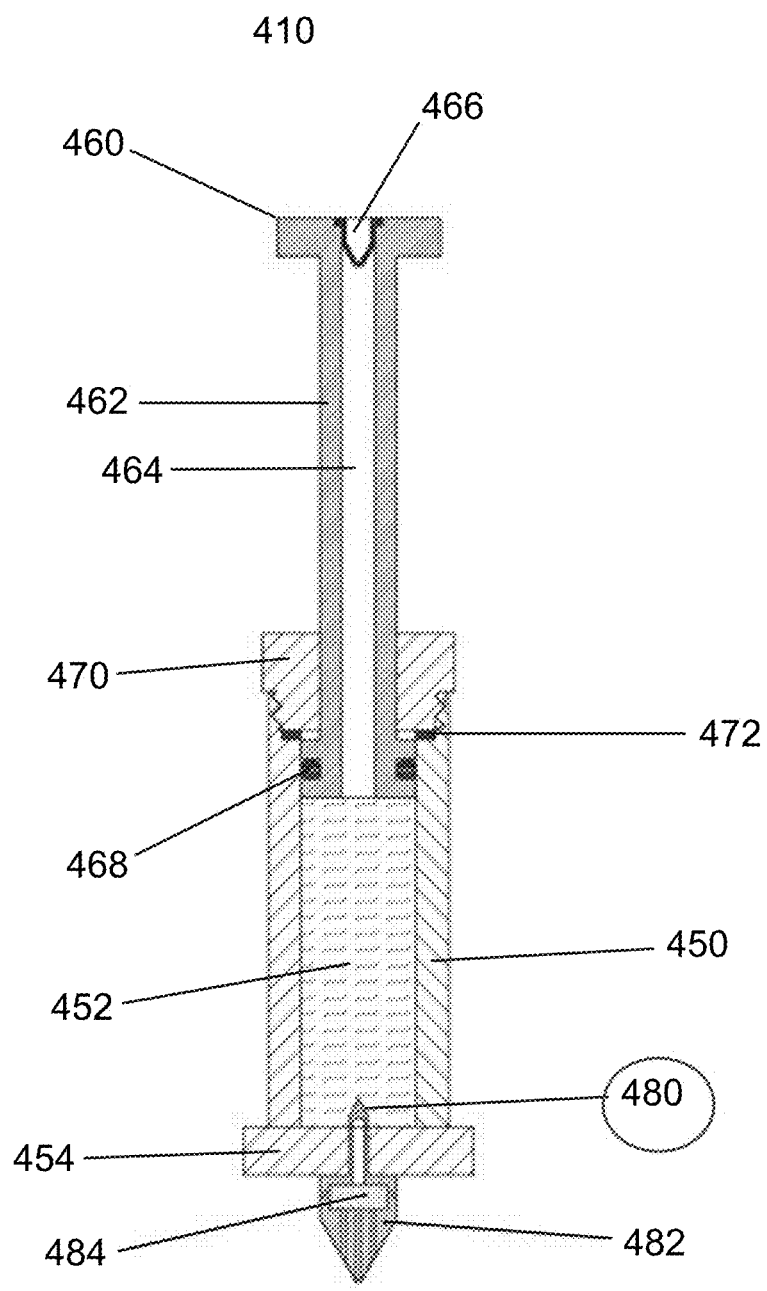
FIG. 4 illustrates a cross-sectional view of an embodiment for a filtration device disclosed herein.
Figure 5:
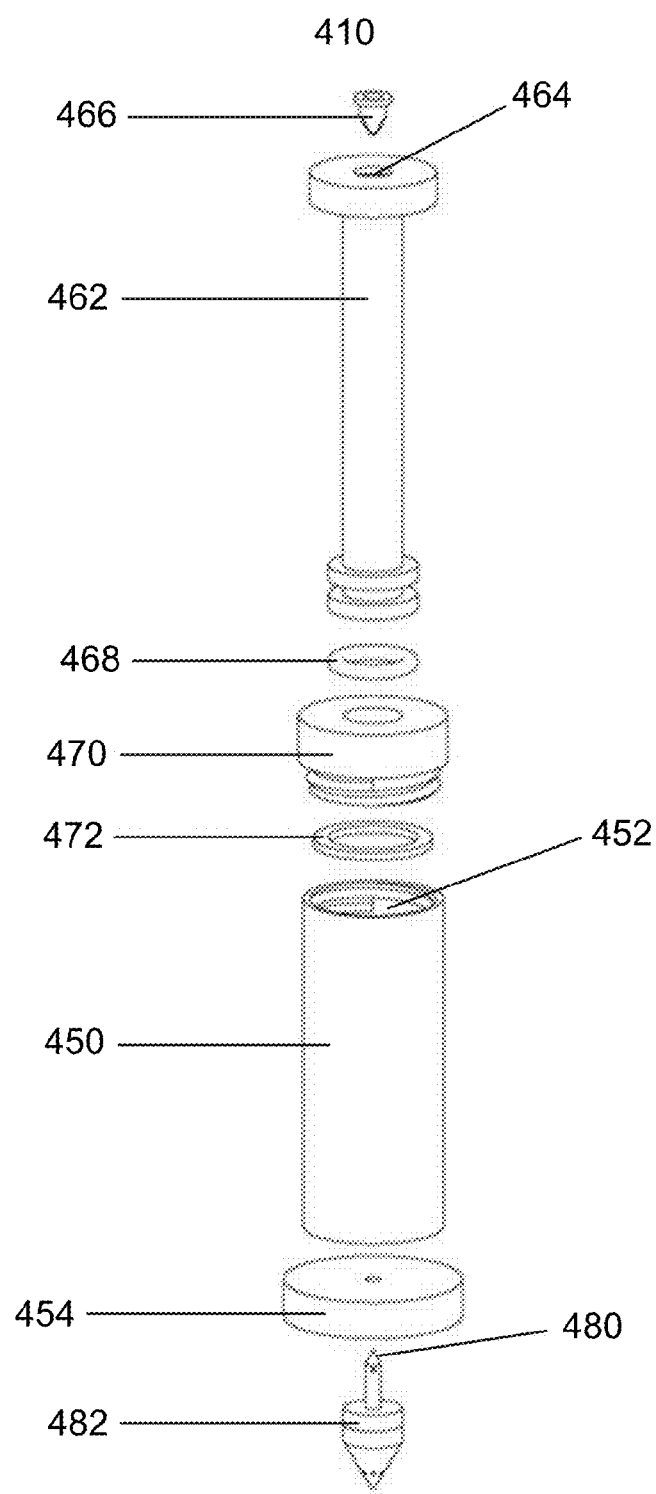
FIG. 5 illustrates a telescopic perspective view of an embodiment for a filtration device disclosed herein.

In another embodiment, filtration device 410 comprises quantitative container 450, plunger device 460, and needle device 480 (FIG. 4). Quantitative container 450 comprises quantitative chamber 452 and base 454 (FIG. 4). Plunger device 460 comprises plunger 462, channel 464, valve 466, plunger O-ring 468, plunger attachment 470 and plunger attachment face seal 472 (FIG. 4). Needle device 480 comprises needle 482 and needle filter 484 (FIG. 4). A telescopic perspective view of this embodiment is shown in FIG. 5.

Figure 6A:
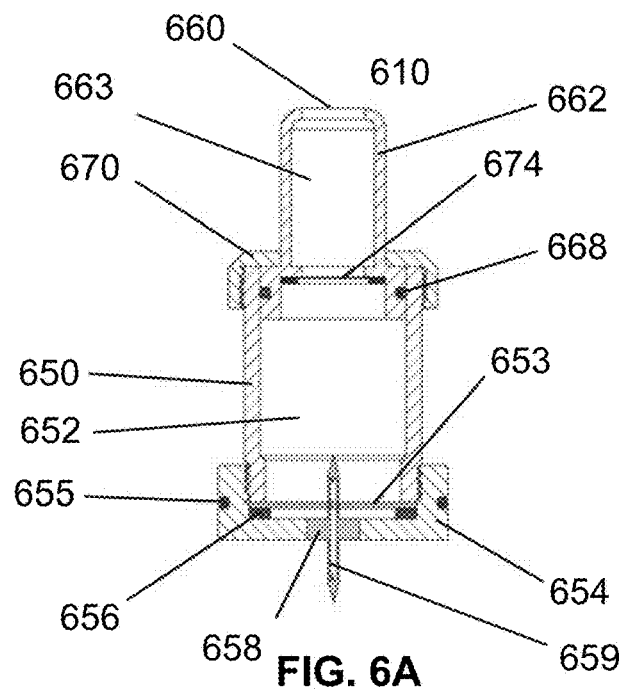
FIG. 6 illustrates a cross-sectional view of an embodiment for a filtration device disclosed herein with FIG. 6A illustrating a cross-sectional view of an embodiment for a quantitative container disclosed herein attached to a plunger device disclosed herein and FIG. 6B illustrating a cross-sectional view of an embodiment for a collection container disclosed herein.
Figure 6B:
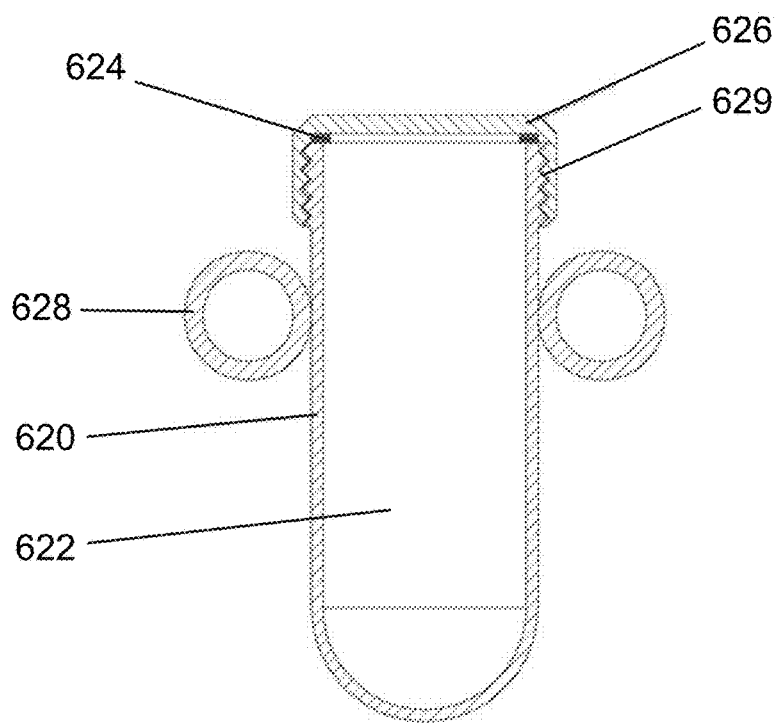
Figure 7:
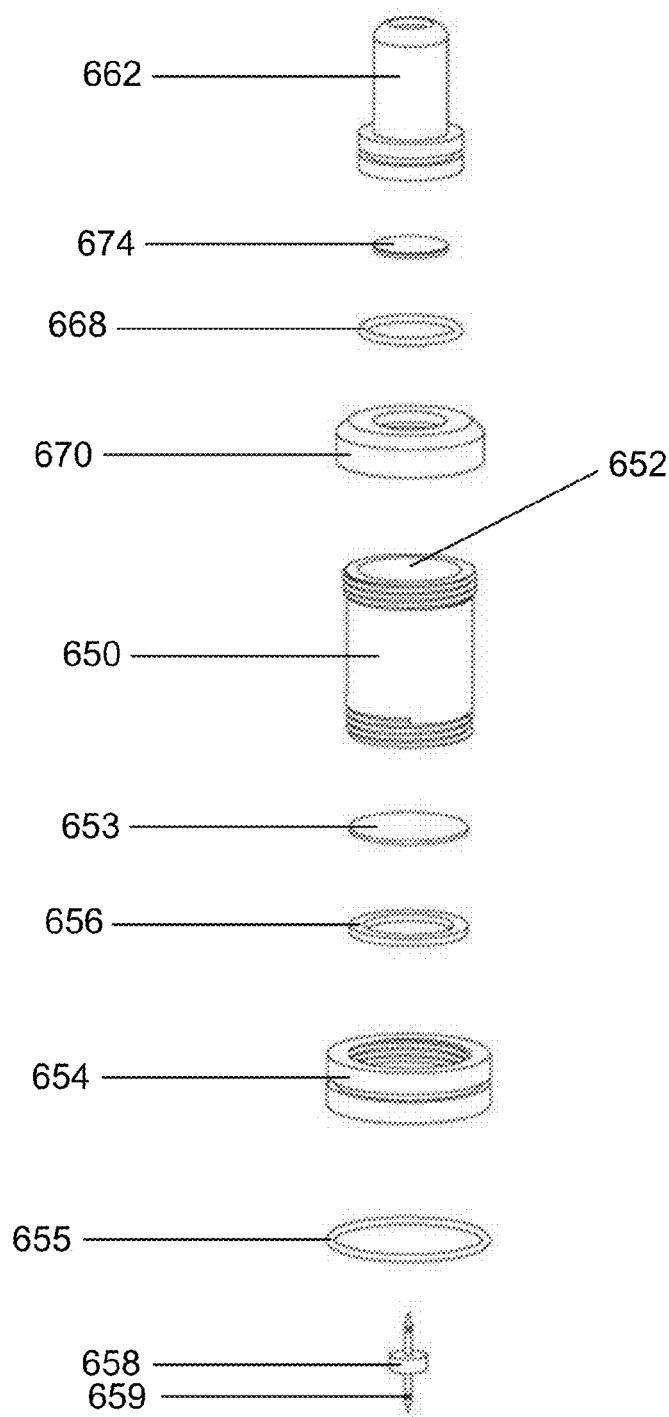
FIG. 7 illustrates a telescopic perspective view of an embodiment for a quantitative container disclosed herein attached to a plunger device disclosed herein.

In another embodiment, filtration device 610 comprises collection container 620, quantitative container 650, and plunger device 660 (FIG. 6A). Collection container 620 comprises collection chamber 622, cap face seal 624, and finger restraint 628 (FIG. 6B). In an aspect of this embodiment, collection chamber cap 626 is attached via screw mechanism 629 to collection container 620. Quantitative container 650 comprises quantitative chamber 652, quantitative filter 653, and base 654 comprising base O-ring 655, base face seal 656, and base needle 658 with needle 659 (FIG. 6B). Plunger device 660 comprises plunger 662, plunger chamber 663, plunger O-ring 668, plunger attachment 670 and plunger filter 674 (FIG. 6A). A telescopic perspective view of this embodiment is shown in FIG. 7.

Figure 8:
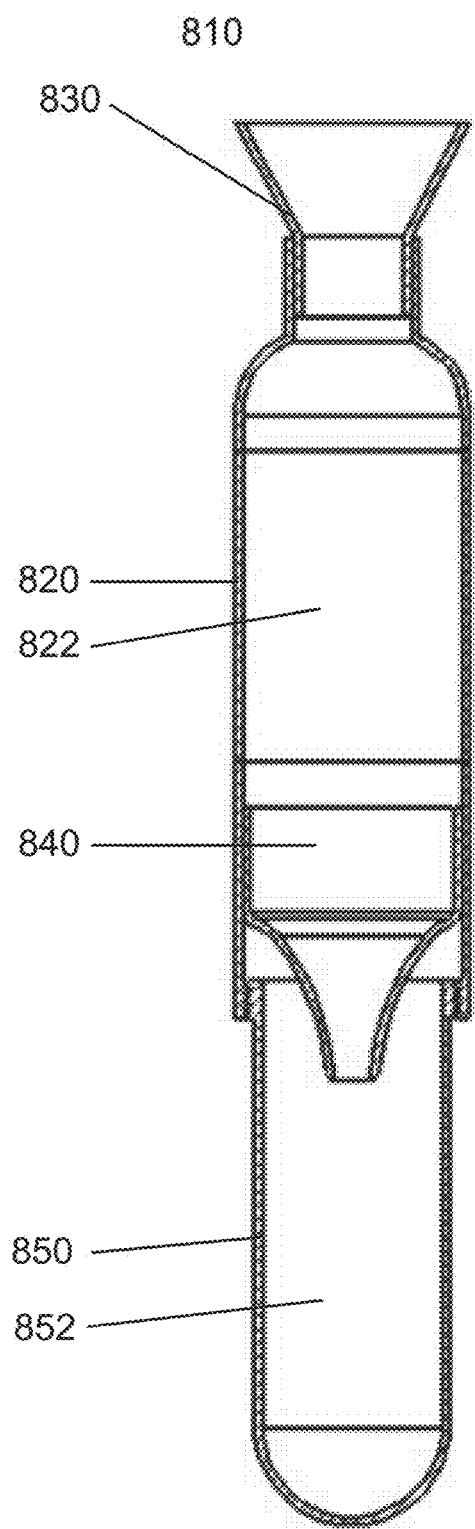
FIG. 8 illustrates a cross-sectional view of an embodiment for a filtration device disclosed herein.

In another embodiment, filtration device 810 comprises collection container 820 and quantitative container 850 (FIG. 8). Collection container 820 comprises collection chamber 822 and filter device 840 (FIG. 8). FIG. 8 also illustrates the placement of collection device 830 to collection container 820. Quantitative container 850 comprises quantitative chamber 852 and base (FIG. 8).

Aspects of the present specification disclose, in part, a sample collection system or kit. A sample collection system or kit disclosed herein may comprise a collection chamber disclosed herein, a quantitative chamber disclosed herein, a waste chamber disclosed herein, a plunger device disclosed herein, a needle device disclosed herein one or more bottles containing processing reagents, and/or any combination thereof. In aspects of this embodiment, a processing reagent disclosed herein includes, without limitation, a wash solution, a lysis solution, a buffered solution, an elution solution, or any combination thereof.

In some embodiments, a sample collection system or kit comprises a collection chamber disclosed herein, a quantitative chamber disclosed herein, a waste chamber disclosed herein, a plunger device disclosed herein, and a needle device disclosed herein. In some embodiments, a sample collection system or kit comprises a collection chamber disclosed herein, a quantitative chamber disclosed herein, a waste chamber disclosed herein, a plunger device disclosed herein, a needle device disclosed herein, and one or more bottles containing processing reagents including, without limitation, a wash solution, a lysis solution, a buffered solution, an elution solution, or any combination thereof.

In some embodiments, a sample collection system or kit comprises a collection chamber disclosed herein, a quantitative chamber disclosed herein, a plunger device disclosed herein, and a needle device disclosed herein. In some embodiments, a sample collection system or kit comprises a collection chamber disclosed herein, a quantitative chamber disclosed herein, a plunger device disclosed herein, and a needle device disclosed herein, and one or more bottles containing processing reagents including, without limitation, a wash solution, a lysis solution, a buffered solution, an elution solution, or any combination thereof.

In some embodiments, a sample collection system or kit comprises a collection chamber disclosed herein, a quantitative chamber disclosed herein, and a waste chamber disclosed herein. In some embodiments, a sample collection system or kit comprises a collection chamber disclosed herein, a quantitative chamber disclosed herein, and a waste chamber disclosed herein, and one or more bottles containing processing reagents including, without limitation, a wash solution, a lysis solution, a buffered solution, an elution solution, or any combination thereof.

Aspects of the present specification disclose, in part, a method of processing a biofluid sample using a filtration device disclosed herein. The device disclosed herein is designed to be used in any environment including point of care use as well as clinical and laboratory settings.

In some embodiments, a method of processing a biofluid sample using a filtration device comprises the steps of a) depositing a biofluid sample into the collection chamber of the filtration device; and b) applying a force to the filtration device whereby the biofluid sample passes through the filter of the collection chamber, a filtered biofluid sample is collected in a quantitative chamber, and a retained biofluid sample is present in the collection chamber.

In some embodiments, a method of processing a biofluid sample using a filtration device comprises the steps of a) depositing a biofluid sample into the collection chamber of the filtration device; and b) applying a force to the filtration device whereby the biofluid sample passes through the filter of the collection chamber, a filtered biofluid sample is collected in a quantitative chamber, and a retained biofluid sample is present in the collection chamber; c) removing the quantitative sample comprising the filtered biofluid sample; d) attaching a plunger device comprising a plunger and a channel to the quantitative chamber; and e) processing the filtered biofluid sample by the addition of suitable reagents using the channel. In aspects of these embodiments, step (e) may be repeated one or more times with the same or different reagents.

In some embodiments, a method of processing a biofluid sample using a filtration device comprises the steps of a) depositing a biofluid sample into the collection chamber of the filtration device; and b) applying a force to the filtration device whereby the biofluid sample passes through the filter of the collection chamber, a filtered biofluid sample is collected in a quantitative chamber, and a retained biofluid sample is present in the collection chamber; c) removing the quantitative sample comprising the filtered biofluid sample; d) attaching a plunger device comprising a plunger and a channel to the quantitative chamber; e) processing the filtered biofluid sample by the addition of suitable reagents using the channel; f) attaching the needle device comprising a needle and porous filter to the quantitative chamber; and g) expelling the processes filtered biofluid sample from the quantitative chamber into a collection tube using the plunger. In aspects of these embodiments, step (e) may be repeated one or more times with the same or different reagents.

In some embodiments, a method of processing a biofluid sample using a filtration device comprises the steps of a) depositing a biofluid sample into the collection chamber of the filtration device; and b) applying a force to the filtration device whereby the biofluid sample passes through the filter of the collection chamber, a filtered biofluid sample is collected in a quantitative chamber, and a retained biofluid sample is present in the collection chamber; c) removing the quantitative sample comprising the filtered biofluid sample; d) attaching a waste chamber to the collection chamber; and e) adding reagents to the collection chamber; and e) applying a force to the filtration device whereby the reagents passes through the filter of the collection chamber and collected in the waste chamber and a processed, retained biofluid sample is present in the collection chamber. In aspects of these embodiments, step (e) may be repeated one or more times with the same or different reagents.

Figure 9G:
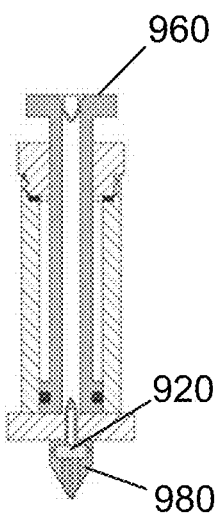
FIG. 9G illustrating expulsion of biofluid sample from quantitative container and retention of bead-bound polynucleotide molecules in the chamber.

In one embodiment, a method of processing a biofluid sample using a filtration device 910 comprises the step of depositing biofluid sample 912 into collection chamber 922 of collection container 920 using collection device 930 (FIG. 9A). After depositing biofluid sample 912 to collection chamber 922, collection device 930 is removed (FIG. 9B) and collection chamber cap 926 is secured to collection container 920 (FIG. 9C). Force is then applied to filtration device 910 in a manner that pushes quantitate device 950 into collection chamber 922 (FIG. 9D). The application of force pushes biofluid sample 912 through filter device 940 thereby separating components or fractions of biofluid sample 912 into a defined volume of filtered components or fraction 916 collected in quantitative chamber 952 and retained biofluid sample comprising host cells 914 remains in collection chamber 922 (FIG. 9D). Quantitative container 850 is then removed from collection container 920 (FIG. 9E) and plunger device 960 and needle device 980 are attached to quantitative container 950 (FIG. 9F). The application of force to plunger device 960 pushes filtered biofluid sample 916 though needle filter 982 further purifying filtered biofluid sample 916 (FIG. 9G).

Figures 10A, 10B, 10C:
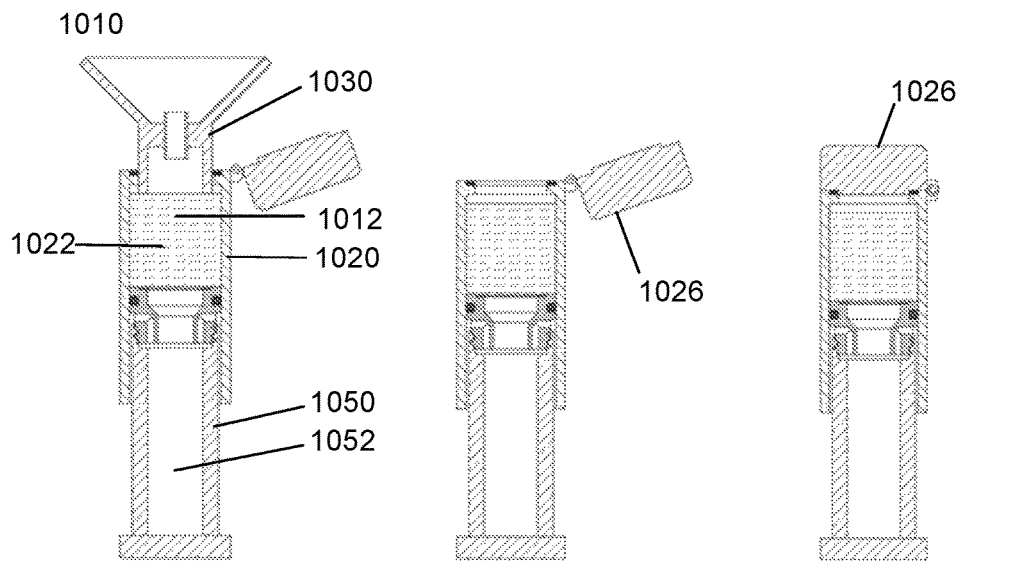
FIG. 10B illustrating removal of collection device.
FIG. 10C illustrating closure of collection chamber by securement of collection chamber cap.
Figures 10D, 10E, 10F:
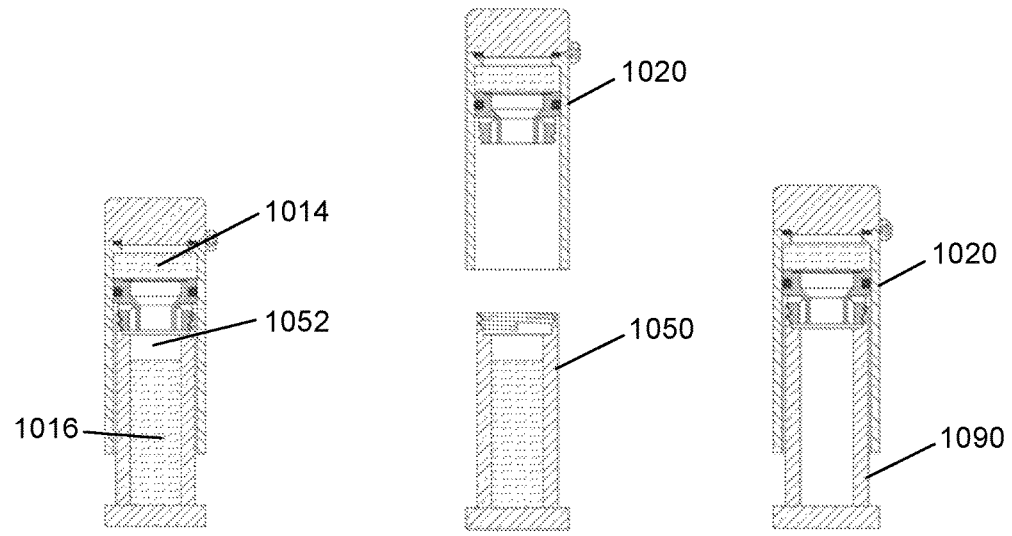
FIG. 10D illustrating filtered biofluid sample contained within quantitative chamber after application of force.
FIG. 10E illustrating removal of quantitative chamber containing filtered biofluid sample from collection container containing retained biofluid sample.
FIG. 10F illustrating attachment of waste container to collection container.

In another embodiment, a method of processing a biofluid sample using a filtration device 1010 comprises the step of depositing biofluid sample 1012 into collection chamber 1022 of collection container 1020 using collection device 1030 (FIG. 10A). After depositing biofluid sample 1012 to collection chamber 1022, collection device 1030 is removed (FIG. 10B) and collection chamber cap 1026 is secured to collection container 1020 (FIG. 10C). Force is then applied to filtration device 1010 in a manner that pushes quantitate container 1050 into collection chamber 1022 (FIG. 10D). The application of force pushes biofluid sample 1012 through filter device 1040 thereby separating components or fractions of biofluid sample 1012 into a defined volume of filtered components or fraction 1016 collected in quantitative chamber 1052 and retained biofluid sample comprising host cells 1014 remains in collection chamber 1022 (FIG. 10D). Quantitative container 1050 is then removed from collection container 1020 (FIG. 10E) and waste container 1090 is attached to quantitative container 1050 (FIG. 10F). A reagent is added to collection chamber 1022 and force is then applied to filtration device 1010 in a manner that pushes waste container 1090 into collection chamber 1022 separating components or fractions 1015 of retained biofluid sample 1014 into waste chamber 1092 (FIG. 10G). Collection chamber cap 1026 is opened (FIG. 10H), additional reagents are added to collection chamber 1022 (FIG. 10I), and collection chamber cap 1026 is closed (FIG. 10J). Force is then applied to filtration device 1010 in a manner that pushes waste container 1090 into collection chamber 1022 separating further components or fractions 1015 of retained biofluid sample 1014 and mixing the flow through with the component or fraction sample already contained in waste chamber 1092 (FIG. 10K).

Figures 11A, 11B, 11C:
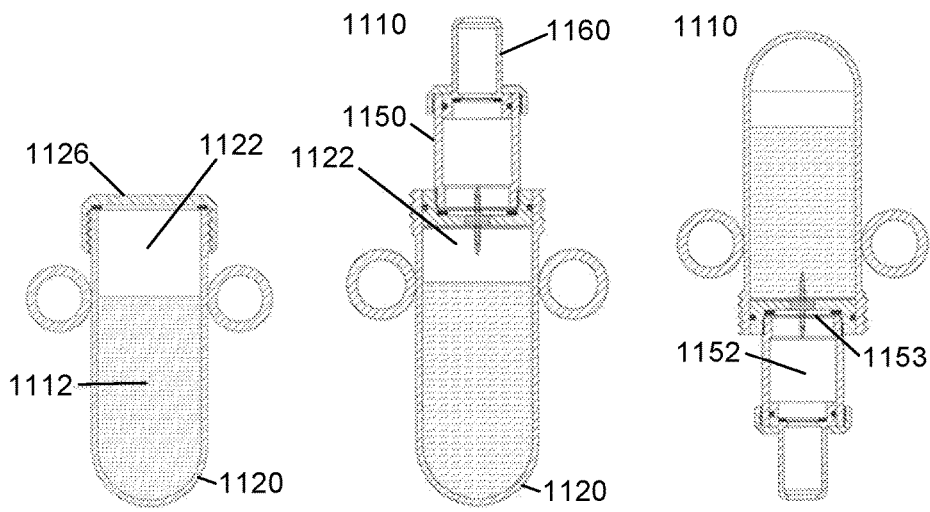
FIG. 11B illustrating removal of collection chamber cap and attachment of quantitative container having plunger device attached.
FIG. 11C illustrating inversion of filtration device.
Figures 11D, 11E:
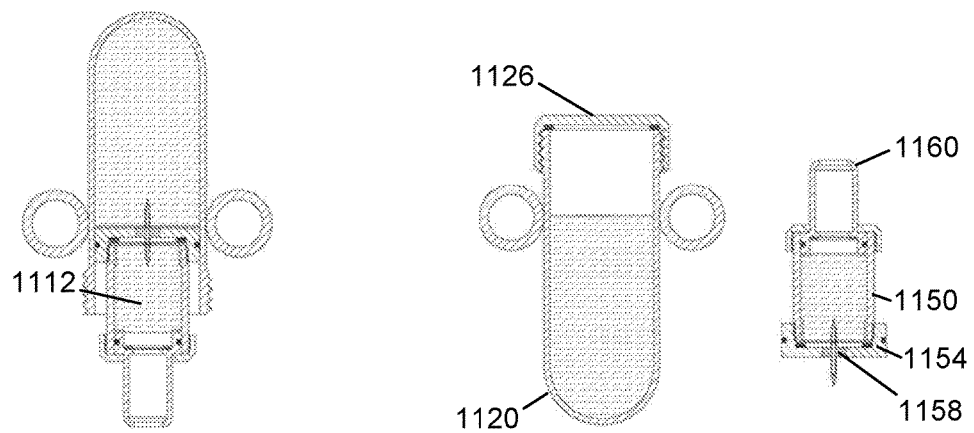
FIG. 11D illustrating transfer of defined volume of biofluid sample to quantitative chamber.
FIG. 11E illustrating removal of collection container from quantitative container having plunger device attached.
Figure 11F:
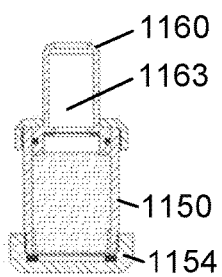
FIG. 11F illustrating removal of base 1054 having needle 1058 and attachment of base 1054 without needle.
Figure 11G:
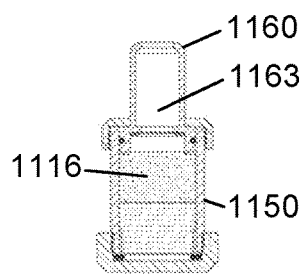
FIG. 11G illustrating separation of fractions of biofluid sample after centrifugation.
Figure 11H:
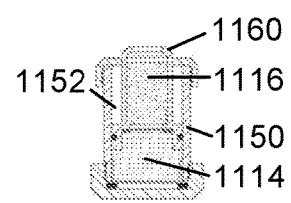
FIG. 11H illustrating filtered biofluid sample contained within plunger chamber after application of force.
Figure 11I:
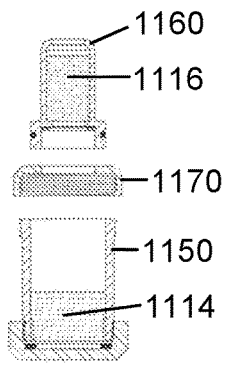
FIG. 11I illustrating removal of plunger device by unsecuring plunger attachment.

In another embodiment, a method of processing a biofluid sample using a filtration device 1110 comprises the step of depositing biofluid sample 1112 into collection chamber 1122 of collection container 1120 (FIG. 11A). After deposition of biofluid sample 1112, collection chamber cap 1126 is removed and quantitative container 1150 (having plunger device 1160 attached to it) is attached to collection container 1120 (FIG. 11B). Filtration device 1110 is inverted (FIG. 11C) and a measured amount of biofluid sample 1112 is collected in quantitative chamber 1152 after being filtered by quantitative filter 1153 (FIG. 11D). After transfer of measured amount of biofluid sample 1112, collection container 1120 is removed from quantitative container 1150 (having plunger device 1160 attached to it) (FIG. 11E). If desired, collection chamber cap 1126 can be attached to collection container 1120 (FIG. 11E). Base 1154 with needle 1158 is removed and base 1154 without needle is secured to quantitative container 1150 (FIG. 11F). Quantitative container 1150 (having plunger device 1160 attached to it) is then placed in centrifuge and components or fractions of measured amount of biofluid sample 1112 separated by application of force (FIG. 11G). Force is then applied to plunger device 1160 in a manner that pushes plunger device 1160 into quantitative chamber 1152 (FIG. 11H). The application of force pushes biofluid sample 1112 through filter device 1140 thereby separating components or fractions of biofluid sample 1112 into a defined volume of filtered components or fraction 916 collected in plunger chamber 1163 and retained biofluid sample comprising host cells 1114 remains in quantitative chamber 1152 (FIG. 11H). Plunger device 1160 is then detached from quantitative container 1150 by removal of plunger attachment 1170 (FIG. 11I). If desired, both filtered components or fraction 1116 and retained biofluid sample 1114 can then be further processed.

In one embodiment, a method of processing a biofluid sample using a filtration device 1210 comprises the step of depositing biofluid sample 1212 into collection chamber 1222 of collection container 1220 using collection device 1230 (FIG. 12A). After depositing biofluid sample 1212 to collection chamber 1222, collection device 1230 is removed and collection chamber cap 1226 is secured to collection container 1220 (FIG. 12B). Force is then applied by squeezing the wall of collection container 1220 (FIG. 12C). The application of force pushes biofluid sample 1212 through filter device 1240 thereby separating components or fractions of biofluid sample 1212 into a defined volume of filtered components or fraction 1216 collected in quantitative chamber 1252 and retained biofluid sample comprising host cells 1214 remains in collection chamber 1222 (FIG. 12C). Quantitative container 1250 is then removed from collection container 1220 and quantitative chamber cap 1276 is attached to quantitative container 1250 (FIG. 12D). Filtered biofluid sample 1216 can then be dispensed from quantitative container 1250 by removing quantitative chamber cap 1276 and applying force by squeezing the wall of quantitative container 1250, thereby dispensing filtered biofluid sample 1216 via nozzle on quantitative chamber dispenser 1278 (FIG. 12F).

Yet another embodiment is illustrated in FIGS. 13A-D. In this embodiment, the filtration device 1310 generally includes a collection container 1320 with a flexible wall 1321 defining a collection chamber 1322 therewithin, a filter device 1340 at the bottom of the collection chamber 1322, a collection device 1330 detachable from the mouth 1327 of the collection chamber 1322, a collection chamber cap 1326 configured to selectively seal the collection chamber 1322, a quantitative chamber dispenser 1378 in fluid communication with the collection chamber 1322 through the filter device 1340 and downstream from the filter device 1340, and a dispenser cap 1379 detachable from the quantitative chamber dispenser 1378. The collection device 1330 is preferably a funnel with a stem 1331 that inserts and attaches within the mouth 1327 of the collection chamber 1322 by frictional engagement, snap feature, other temporary attachment means. The collection device 1330 is sufficiently sized and shaped to collect a biofluid sample 1312, e.g., saliva, urine, or other bodily fluid. The biofluid sample 1312 is deposited into the collection device 1330 and drained into the collection chamber 1322 through the stem 1331 inserted into the mouth 1327. Generally, during the collection of the biofluid sample 1312, the dispenser cap 1379 is seated over the quantitative chamber dispenser 1378 to seal the orifice 1377. The dispenser cap 1379 may be connected to the quantitative chamber dispenser 1378 or other part of the filtration device 1310 by a living hinge, lanyard, or other connecting device to keep the dispenser cap 1379 in proximity to the filtration device 1310. Once the biofluid sample 1312 is collected, the collection device 1330 is detached, and the collection chamber cap 1326 is sealed to the mouth 1327 to seal the collection chamber 1322 from above. The collection chamber cap 1326 may be any variety of caps, such as the bung stopper type cap connected to the collection container 1320 by a living hinge, lanyard, or other connection means.

Once the biofluid sample 1312 has been collected and contained with the collection chamber 1322, and the collection chamber 1322 sealed by closing the collection chamber cap 1326, the user applies a pinching or squeezing force on the collection chamber 1322 causing the flexible wall 1321 to collapse and reduce the volume of the collection chamber 1322. The reduction in volume and accompanying increase in pressure forces the biofluid sample 1312 through the filter device 1340 which captures much, if not all, the debris 1341 within the biofluid sample 1312. The filtered biofluid sample 1316 is collected within the nozzle 1375 of the quantitative chamber dispenser 1378 downstream of the filter device 1340. Upon detachment of the dispenser cap 1379 from the collection container 1320, the user may selectively apply pressure to the flexible wall 1321 of the collection container 1320 to force the flow of the filtered biofluid sample 1316 out of the orifice 1377, preferably in a predetermined droplet size controlled at least in part by the orifice 1377 diameter. The droplets of filtered biofluid sample 1316 may be instilled on a lateral flow device 1351, as illustrated in FIG. 13D, or collected for later analysis or immediate freezing in a storage device, or applied to a diagnostic device. The volume of each drop of filtered biofluid sample 1316 is controlled by the diameter of the orifice. In one example embodiment, six drops can equal approximately 100 microliters, but may vary from 1 microliter to 200 microliters.

The advantage of filtering the biofluid sample 1312 is that a typical biofluid sample 1312 has a large number of contaminants; for example, saliva generally has food and other debris and detritus, as well as bacteria and human cells that negatively affect the assay. Further advantages include the elimination or reduction of centrifugation and cold chain logistics. The filter device 1340 is selected to remove undesired components within the feed (biofluid sample 1312) to produce a higher purity filtrate (filtered biofluid sample 1316). Squeezing the collection chamber 1322 creates the necessary difference in pressure across the filter device 1340 to force the feed through the filter device 1340. Diseases with detectable biomarkers within the filtered biofluid sample 1316 (such as in salivary analytes) are detectable using the present device 1310, such as malaria, periodontal disease, and cortisol stress, without interference from contaminants. The types of analysis may include, but are not limited to, human and bacterial DNA purification and quantitation by RT-PCR and a biomarker assay. Two common salivary biomarkers are cortisol (a steroid) and interleukin 1β (a protein).

A kit may include the filter device 1310, collection device 1330 and a container of cell lysis solution that may be placed in fluid communication with either the orifice 1377 or the mouth 1327 for introducing the cell lysis solution into the collection chamber 1322. In one method, the user may apply a squeezing force on the flexible wall 1321 of the collection chamber 1322 to force out substantially all the biofluid sample 1312, leaving the debris 1341 in or on the filter device 1340. The orifice 1377 is submerged in the cell lysis solution or the cell lysis solution container is connected to the quantitative collection dispenser 1378. The user releases the squeezing force applied to the collection chamber 1322 so that the wall 1321 is permitted to rebound to its original shaped, thereby producing a vacuum within the collection chamber 1322 that draws the cell lysis solution through the filter device 1340 and into the collection chamber 1322, where the cell lysis solution extract DNA and such from the cells remaining within the collection chamber 1322. Once the cells have been processed within the cell lysis solution, the solution may be pushed back through the filter for collection and analysis.

The present filtering device 1310 provides a rapid, cost effective, non-invasive collection and clean-up of saliva (e.g., reduction of contaminants, matrix effects, etc.) for early detection of Malaria biomarkers (e.g., pfHRP2, etc.). Clean or filtered saliva offers several advantages over blood no cultural and/or religious biases associated with collection of blood, a reduced biohazard to worker, non-invasive, easy and in-field usable, and it requires minimal or no training. This permits the early and accurate diagnosis of Malaria at the point-of-care, within the recommended 24 hour window after the onset of fever. It is important to process a biofluid sample to eliminate biomarker stability issues, contaminants (e.g., cells, mucins, etc.), and matrix effects (e.g., viscosity), which is easily carried out in the field using the present filtering device 1310, without the use of cold chain logistics or centrifugation. Using the present filtering device 1310, in less than 10 seconds after collection the viscosity is significantly reduced and the saliva filtered which readies the sample for immediate testing.

Aspects of the present specification may also be described as follows:

1. A filtration device comprising
    a) a collection container comprising a collection chamber and a filter device comprising a filter mount, a filter, a port, a one-way check valve, and O-ring; and
    b) a quantitative container comprising a quantitative chamber and a base; wherein the quantitative container is removably attached to the collection container and wherein the quantitative container is configured to move into the collection chamber upon the application of force.
2. The filtration device according to embodiment 1, wherein the collection container includes a collection chamber cap attached to the collection container.
3. The filtration device according to embodiment 1 or 2, wherein the collection container includes a collection chamber cap not attached to the collection container.
4. The filtration device according to any one of embodiments 1-3, wherein the base is removable.
5. The filtration device according to any one of embodiments 1-4, wherein the filter has a pore size of about 0.2 μm to about 50.0 μm.
6. The filtration device according to any one of embodiments 1-5, wherein the quantitative chamber has a volume of about 0.5 mL to about 5.0 mL.
7. The filtration device according to any one of embodiments 1-6, wherein the quantitative chamber has a volume of 1 mL.
8. A filtration device comprising
    a) a quantitative container comprising a quantitative chamber and a base; and
    b) a plunger device comprising a plunger including a channel, a valve, and a plunger O-ring, and a plunger attachment including a plunger attachment face seal.
    wherein the plunger device is removably attached to the quantitative container and wherein the plunger device is configured to move into the quantitative chamber upon the application of force.
9. The filtration device according to embodiment 8, wherein the base is removable.
10. The filtration device according to embodiment 8 or 9, wherein the quantitative chamber has a volume of about 0.5 mL to about 5.0 mL.
11. The filtration device according to any one of embodiments 8-10, wherein the quantitative chamber has a volume of 1 mL.
12. The filtration device according to any one of embodiments 8-11, wherein the valve is a duck-bill valve.
13. The filtration device according to any one of embodiments 8-12, further comprising a needle device attached to the base.
14. The filtration device according to embodiment 13, wherein the needle device includes a needle having a diameter between about 0.1 mm to about 2.0 mm.
15. The filtration device according to embodiment 13 or 14, wherein the needle device includes a needle filter.
16. The filtration device according to embodiment 15, wherein the needle filter has a pore size of about 0.2 μm to about 50.0 μm.
17. A filtration device comprising
    a) a quantitative container comprising a quantitative chamber, a quantitative filter, and a base including a base needle; and
    b) a plunger device comprising a plunger including a plunger O-ring, a plunger filter, a plunger chamber, and a plunger attachment including a plunger attachment face seal.
    wherein the plunger device is removably attached to the quantitative container and wherein the plunger device is configured to move into the quantitative chamber upon the application of force.
18. The filtration device according to embodiment 17, wherein the quantitative chamber has a volume of about 0.5 mL to about 5.0 mL.
19. The filtration device according to embodiment 18, wherein the quantitative chamber has a volume of 1 mL.
20. The filtration device according to any one of embodiments 17-19, wherein the quantitative filter has a pore size of about 0.2 μm to about 50.0 μm.
21. The filtration device according to any one of embodiments 17-20, wherein the base needle has a diameter between about 1.0 mm to about 10.0 mm.
22. The filtration device according to any one of embodiments 17-21, wherein the base needle includes a base needle filter.
23. The filtration device according to any one of embodiments 17-22, wherein the base needle filter has a pore size of about 0.2 μm to about 50.0 μm.
24. The filtration device according to any one of embodiments 17-23, wherein the plunger chamber has a volume of about 0.5 mL to about 5.0 mL.
25. The filtration device according to embodiment 24, wherein the plunger chamber has a volume of 1 mL.
26. The filtration device according to any one of embodiments 17-25, wherein the plunger filter has a pore size of about 0.2 μm to about 50.0 μm.
27. The filtration device according to any one of embodiments 17-26, further comprising a collection container comprising a collection chamber, wherein the collection container is removably attached to the quantitative container.
28. The filtration device according to embodiment 27, wherein the collection chamber has a volume of about 0.5 mL to about 10.0 mL.
29. The filtration device according to embodiment 28, wherein the collection chamber has a volume of about 1 mL to about 5.0 mL.
30. A filtration device comprising
    a) a collection container comprising a collection chamber and a filter device comprising a filter mount, a filter, and O-ring; and
    b) a quantitative container comprising a quantitative chamber; wherein the quantitative container is removably attached to the collection container.

31. The filtration device according to embodiment 30, wherein the collection container includes a collection chamber cap attached to the collection container.

32. The filtration device according to embodiment 30 or 31, wherein the collection container includes a collection chamber cap not attached to the collection container.

33. The filtration device according to any one of embodiments 30-32, wherein the filter has a pore size of about 0.2 µm to about 50.0 µm.

34. The filtration device according to any one of embodiments 30-33, wherein the quantitative chamber has a volume of about 0.5 mL to about 5.0 mL.

35. The filtration device according to any one of embodiments 30-34, wherein the quantitative chamber has a volume of 1 mL.

36. The filtration device according to any one of embodiments 30-35, wherein the quantitative chamber further comprises a quantitative chamber dispenser.

37. The filtration device according to any one of embodiments 1-36, wherein the collection container is designed to have rigid walls.

38. The filtration device according to any one of embodiments 1-36, wherein the collection container is designed to have flexible walls.

39. A method of processing a biofluid sample using a filtration device as defined in any one of embodiments 1-16 or 30-38, the method comprising the steps of:
    a) depositing a biofluid sample into the collection chamber of the filtration device; and
    b) applying a force to the filtration device whereby the biofluid sample passes through the filter of the collection chamber, a defined volume of filtered biofluid sample is collected in the quantitative chamber, and a retained biofluid sample remains in the collection chamber.

40. The method according to embodiment 39, wherein the force is applied in a manner that moves a quantitation chamber into a collection chamber of a collection container 41. The method according to embodiment 39, wherein the force is applied in a manner that squeezes the walls of a quantitative container.

41. A method of processing a biofluid sample using a filtration device as defined in any one of embodiments 1-16 or 30-38, the method comprising the steps of:
    a) depositing a biofluid sample into the collection chamber of the filtration device;
    b) applying a force to the filtration device whereby the biofluid sample passes through the filter of the collection chamber, a filtered biofluid sample is collected in the quantitative chamber, and a retained biofluid sample is present in the collection chamber;
    c) removing the quantitative sample comprising the filtered biofluid sample;
    d) attaching a plunger device comprising a plunger and a channel to the quantitative chamber; and
    e) processing the filtered biofluid sample by the addition of suitable reagents using the channel.

42. The method according to embodiment 41, wherein step (e) is repeated one or more times with the same or different reagents.

43. The method according to embodiment 41 or 42, wherein the force is applied in a manner that moves a quantitation chamber into a collection chamber of a collection container 44. The method according to embodiment 41 or 42, wherein the force is applied in a manner that squeezes the walls of a quantitative container.

45. A method of processing a biofluid sample using a filtration device as defined in any one of embodiments 1-16 or 30-38, the method comprising the steps of:
    a) depositing a biofluid sample into the collection chamber of the filtration device;
    b) applying a force to the filtration device whereby the biofluid sample passes through the filter of the collection chamber, a filtered biofluid sample is collected in a quantitative chamber, and a retained biofluid sample is present in the collection chamber;
    c) removing the quantitative sample comprising the filtered biofluid sample;
    d) attaching a plunger device comprising a plunger and a channel to the quantitative chamber;
    e) processing the filtered biofluid sample by the addition of suitable reagents using the channel;
    f) attaching the needle device comprising a needle and porous filter to the quantitative chamber; and
    g) expelling the processes filtered biofluid sample from the quantitative chamber into a collection tube using the plunger.

46. The method according to embodiment 38, wherein step (e) may be repeated one or more times with the same or different reagents.

47. The method according to embodiment 45 or 46, wherein the force is applied in a manner that moves a quantitation chamber into a collection chamber of a collection container 48. The method according to embodiment 45 or 46, wherein the force is applied in a manner that squeezes the walls of a quantitative container.

49. A method of processing a biofluid sample using a filtration device, the method comprising the steps of:
    a) attaching a collection container comprising a biofluid sample to the filtration device as defined in any one of embodiments 17-29, 37 or 38;
    b) transferring an amount of the biofluid sample to the quantitative chamber;
    c) removing the collection container from the filtration device;
    d) applying a force to the filtration device whereby the biofluid sample passes through the quantitative filter of the quantitative container, a filtered biofluid sample is collected in the plunger chamber, and a retained biofluid sample remains in the quantitative chamber.

50. The method according to embodiment 42, further comprising the step of applying a force to the filtration device whereby the biofluid sample is separated into two or more fractions within the quantitative chamber, the step being performed before step (d).

51. The method according to embodiment 49 or 50, wherein the force is applied in a manner that moves a quantitation chamber into a collection chamber of a collection container 52. The method according to embodiment 49 or 50, wherein the force is applied in a manner that squeezes the walls of a quantitative container.

53. A method of processing a biofluid sample using a filtration device as defined in any one of embodiments 1-16 or 30-38, the method comprising the steps of:
    a) depositing a biofluid sample into the collection chamber of the filtration device; and
    b) applying a force to the filtration device whereby the biofluid sample passes through the filter of the collection chamber, a defined volume of filtered biofluid sample is collected in the quantitative chamber, and a retained biofluid sample remains in the collection chamber.
54. The method according to embodiment 53, further comprising step c) removing the quantitative container from the collection container and attaching a quantitative chamber dispenser to the quantitative container.
55. The method according to embodiment 54, further comprising step d) applying a force to the quantitative container whereby the filtered biofluid sample passes from collection chamber to the outside environment.
56. The method according to any one of embodiments 53-55, wherein the force in step b) is in a manner that squeezes the walls of a quantitative container.
57. The method according to embodiment 55, wherein the force in step d) is in a manner that squeezes the walls of a quantitative container.
58. A system for processing a biofluid sample, the system comprising a filtration device as defined in any one of embodiments 1-38, or:
    a) a collection container comprising a collection chamber and a filter device comprising a filter mount, a filter, a port, and O-ring;
    b) a quantitative container comprising a quantitative chamber and base; and
    c) a plunger device comprising a plunger including a channel, a valve and a plunger O-ring, and a plunger attachment including a plunger attachment face seal.
59. The system according to embodiment 58, wherein the base is removable.
60. The system according to embodiment 58 or 59, further comprising a needle device comprising a needle and a needle filter.
61. The system according to any one of embodiments 58-60, further comprising a waste container comprising a waste chamber.
62. A system for processing a biofluid sample, the system comprising a filtration device as defined in any one of embodiments 1-38, or:
    a) a collection container comprising a collection chamber and a filter device comprising a filter mount, a filter, a port, and O-ring;
    b) a quantitative container comprising a quantitative chamber and base;
    c) a waste container comprising a waste chamber;
    d) a plunger device comprising a plunger including a channel, a valve and a plunger O-ring, and a plunger attachment including a plunger attachment face seal; and
    e) a needle device comprising a needle and a needle filter.
63. A system for processing a biofluid sample, the system comprising a filtration device as defined in any one of embodiments 1-38, or:
    a) a quantitative container comprising a quantitative chamber and a base including a needle;
    b) a plunger device comprising a plunger including a plunger O-ring, a plunger filter, a plunger chamber, and a plunger attachment including a plunger attachment face seal; and
    c) a base without needle.
64. The system according to embodiment 63, further comprising a collection container comprising a collection chamber and collection chamber cap.
65. A system for processing a biofluid sample, the system comprising a filtration device as defined in any one of embodiments 1-38, or:
    a) a collection container comprising a collection chamber and collection chamber cap;
    b) a quantitative container comprising a quantitative chamber and a base including a needle;
    c) a plunger device comprising a plunger including a plunger O-ring, a plunger filter, a plunger chamber, and a plunger attachment including a plunger attachment face seal; and
    d) a base without needle.
66. A system for processing a biofluid sample, the system comprising a filtration device as defined in any one of embodiments 1-38, or:
    a) a collection container comprising a collection chamber and a filter device comprising a filter mount, a filter, and O-ring; and
    b) a quantitative container comprising a quantitative chamber and a quantitative chamber dispenser.
67. The system according to embodiment 66, wherein the collection container is designed to have flexible walls.
68. The system according to embodiment 66 or 67, wherein the quantitative container is designed to have flexible walls.

EXAMPLES

The following non-limiting examples are provided for illustrative purposes only in order to facilitate a more complete understanding of representative embodiments now contemplated. These examples should not be construed to limit any of the embodiments described in the present specification, including those pertaining to the filtration device disclosed herein, or methods or uses of the filtration device disclosed herein.

Example 1

This example demonstrates that depending on the filter used, different types of component separation can be achieved.

A user prepared a filtration device by attaching a funnel to the opening of a collection chamber of a filtration device comprising a collection chamber and a quantitative chamber. The filtration device contained a PVDF membrane with a mean pore size of 5 µm (Millipore). The user deposited saliva into the collection chamber using the attached funnel. After the saliva was deposited into the collection chamber, the user removed the funnel and attached a collection chamber cap to the opening, thereby sealing the collection chamber. The user then pushed the quantitative chamber into the collection chamber, forcing a defined 1 mL volume of saliva to pass through the filter. After filtration, both the filtered saliva sample and retained saliva sample were assayed for the presence of bacterial and human cells. The results indicate that the retained saliva sample after filtration comprised only 17% the bacterial content (i.e., the amount which remained bound to the filter), while the remainder of the bacterial content passed through the filter. Conversely, the retained saliva sample comprised over 99% of the human cell content (i.e., the amount which remained bound to the filter), while only about 0.7% of the human cell content passed through the filter. These results indicate that a PVDF membrane with a mean pore size of 5 µm was sufficient to separate bacterial contamination from human cells which would be critical for procedures, such as, e.g., genotyping using DNA sequences techniques.

A user prepared a filtration device by attaching a funnel to the opening of a collection chamber of a filtration device comprising a collection chamber and a quantitative chamber. The filtration device contained a cellulose membrane with a mean pore size of 5 µm (Sartorius). The user deposited saliva into the collection chamber using the attached funnel. After the saliva was deposited into the collection chamber, the user removed the funnel and attached a collection chamber cap to the opening, thereby sealing the collection chamber. The user then pushed the quantitative chamber into the collection chamber, forcing a defined 1 mL volume of saliva to pass through the filter. After filtration, both the filtered saliva sample and retained saliva sample were assayed for the presence of bacterial and human cells. The results indicate that the retained saliva sample comprised 96.5% of the bacterial content (i.e., the amount which remained bound to the filter), with only a small amount (about 3.5%) of the bacterial content passed through the filter. Similarly, the retained saliva sample comprised over 98% of the human cell content (i.e., the amount which remained bound to the filter), while only about 1.6% of the human cell content passed through the filter. These results indicate that a cellulose membrane with a mean pore size of 5 µm was very effective at filtering all cellular content from whole saliva, but not effective in separating bacterial and human cells. Thereby such a filter membrane would not be suitable for genotyping applications where purity of human DNA is of paramount importance. However, it would be critical for procedures, such as, e.g., assays designed to detect the presence of a compound (analyte) where presence of cells can interfere and lead to false positive results.

Example 2

This example describes how to use a filtration device disclosed herein to filter a biofluid sample. A user prepares a filtration device by attaching a funnel to the opening of a collection chamber of a filtration device comprising a collection chamber and a quantitative chamber. The user hands the prepared filtration device to a subject and asks the subject to deposit saliva into the collection chamber using the attached funnel. After the saliva is deposited into the collection chamber, the user removes the funnel and attaches a collection chamber cap to the opening, thereby sealing the collection chamber. The user then pushes the quantitative chamber into the collection chamber, forcing a defined 1 mL volume of saliva to pass through the filter, and the filtered saliva is collected in the quantitative chamber of the quantitative container. The filter retains debris and other contaminating material behind in the collection chamber. After filtration, a defined volume of filtered saliva sample is collected in the quantitative chamber and a retained saliva sample comprising host cells is retained on the filter of the collection chamber.

The filtered saliva sample can now be used to any number of diagnostic assays used to detect the presence or absence of a compound or compounds. For example, the filtered saliva sample can be tested for the presence of cortisol, testosterone, leptin or C-Reactive Protein (CRP). For example, salivary cortisol was shown to be a good prognostic indicator of Major depressive disorder (MD) in the youth population at large that can aid the detection of at-risk groups. MD is a debilitating public mental health problem with severe societal and personal costs attached. Dysregulated cortisol rhythms and elevated morning and evening cortisol have consistently been reported as a risk factor for, or consequence of, MD. By facilitating filtering of whole saliva during early AM and late night in at the point-of-care, an individual can forgo regular visits to the clinic for sample collection.

A device that simultaneously achieves separation of debris and other contaminating material from saliva at point-of-care has broad utility in life sciences. It allows users to assess levels of a large number of compounds useful as markers in the diagnosis of a wide variety of disease all with one device. Furthermore, the quantitative collection of cell-free saliva will facilitate standardization of all diagnostic assays in that individual and comparing it to other individuals for purposes of targeted therapy or epidemiological studies.

Example 3

This example describes how to use a filtration device disclosed herein to filter a biofluid sample. A user prepares a filtration device by attaching a funnel to the opening of a collection chamber of a filtration device comprising a collection chamber and a quantitative chamber. The user hands the prepared filtration device to a subject and asks the subject to deposit saliva into the collection chamber using the attached funnel. After the saliva is deposited into the collection chamber, the user removes the funnel and attaches a collection chamber cap to the opening, thereby sealing the collection chamber. The user then squeezes the wall of the collection container, forcing saliva to pass through the filter, and the filtered saliva is collected in the quantitative chamber of the quantitative container. After the filtration, a volume of filtered saliva sample is collected in the quantitative chamber and a retained saliva sample comprising host cells, debris and other contaminating material is retained on the filter of the collection chamber.

The filtered saliva sample can now be used to any number of diagnostic assays used to detect the presence or absence of a compound or compounds as described in Example 2.

A device that simultaneously achieves separation of debris and other contaminating material from saliva at point-of-care has broad utility in life sciences. It allows users to assess levels of a large number of compounds useful as markers in the diagnosis of a wide variety of disease all with one device. Furthermore, the quantitative collection of cell-free saliva will facilitate standardization of all diagnostic assays in that individual and comparing it to other individuals for purposes of targeted therapy or epidemiological studies.

Example 4

This example describes how to use a filtration device disclosed herein to filter a biofluid sample. A user prepares a filtration device by attaching a funnel to the opening of a collection chamber of a filtration device comprising a collection chamber and a quantitative chamber. The user hands the prepared filtration device to a subject and asks the subject to deposit saliva into the collection chamber using the attached funnel. After the saliva is deposited into the collection chamber, the user removes the funnel and attaches a collection chamber cap to the opening, thereby sealing the collection chamber. The user then pushes the quantitative chamber into the collection chamber, forcing a defined 1 mL volume of saliva to pass through the filter that allows contaminating bacteria and/or infectious agents smaller than the filter pore size to pass through, while retaining human cells behind in the collection chamber. After the filtration, a defined volume of filtered saliva sample (containing contaminating bacteria and/or any infectious agents) is collected in the quantitative chamber and a retained saliva sample comprising host cells is retained on the filter of the collection chamber.

To process the filtered saliva sample in the quantitative chamber, the user removes the quantitative chamber comprising the filtered saliva sample and attaches a plunger device comprising a plunger and channel as disclosed herein. The user then adds reagents such as lysis buffer with DNA binding beads to the saliva sample using the channel running through the plunger and mixes the added reagents and saliva by inverting and mixing the contents, allowing DNA released from the infectious agents in the chamber to bind to the beads. Depending on the processing desired, the mixed sample may then be chilled on ice, heated in a water bath or incubator, or have additional reagents added.

To isolate DNA from this mixture, the user can add a needle device disclosed herein. The user attaches the needle device to the bottom of the quantitative chamber and then expels the mixed sample containing the bead-bound DNA into a collection tube. The bead-bound DNA captured on the filter is then washed and eluted using reagents and methods known in the art. The processed filtered saliva sample can then be used or further processed or stored for subsequent use or further processing.

To process the retained saliva sample in the collection chamber containing human cells, the user removes the quantitative chamber comprising the filtered saliva sample and attaches a waste chamber as disclosed herein to the collection chamber. The user then pushes the waste chamber into the collection chamber to filter any remaining biofluid sample contained in the collection chamber. The user then removes the collection chamber cap, adds reagents (such as wash buffer) to the collection chamber containing pure human cells, and re-attaches the collection chamber cap and repeats the filtration process, ensuring cleansing of the human cells from any remaining contaminating bacterial and/or infectious agents. The washing can be done two or more times or as required to purify the human cells from remnant contaminating bacterial and/or infectious agents. Depending on the processing desired, the retained saliva sample with reagents may then be chilled on ice, heated in a water bath or incubator, and/or have addition reagents added. Depending on the processing desired, after processing of the retained saliva sample is complete, the user may then re-suspend the human cell on the filter in re-suspension buffered solution and transfer the elute into a clean tube. The eluted human cells can then be used or further processed or stored for subsequent use or further processing in downstream applications such as genotyping A device that simultaneously achieves separation of human cells from contaminating bacteria and/or potential infectious agents in saliva at the point-of-care has broad utility in life sciences. It allows users to assess human host genotype information as well as quantification and/or identification of potential infections associated with that individual, all with one device. Furthermore, the quantitative collection of cell-free saliva will facilitate standardization of all assays for determining infections in that individual and comparing it to other individuals for purposes of targeted therapy or epidemiological studies.

Example 5

This example describes how to use a filtration device disclosed herein to filter a biofluid sample. A user prepares a filtration device by attaching a funnel to the opening of a collection chamber of a filtration device comprising a collection chamber and a quantitative chamber. The user hands the prepared filtration device to a subject and asks the subject to deposit saliva into the collection chamber using the attached funnel. After the saliva is deposited into the collection chamber, the user removes the funnel and attaches a collection chamber cap to the opening, thereby sealing the collection chamber. The user then squeezes the wall of the collection container, forcing saliva to pass through the filter, and the filtered saliva is collected in the quantitative chamber of the quantitative container. After the filtration, a defined volume of filtered saliva sample is collected in the quantitative chamber and a retained saliva sample comprising host cells, debris and other contaminating material is retained on the filter of the collection chamber. The filter used will allow contaminating bacteria and/or infectious agents smaller than the filter pore size to pass through, while retaining human cells behind in the collection chamber. After filtration, a volume of filtered saliva sample (containing contaminating bacteria and/or any infectious agents) is collected in the quantitative chamber and a retained saliva sample comprising host cells is retained on the filter of the collection chamber.

Example 6

This example describes how to use a filtration device disclosed herein to filter a biofluid sample. A user adds a whole blood sample to a collection chamber of a filtration device comprising a collection chamber and a quantitative chamber. After the blood sample is deposited into the collection chamber, the user attaches a quantitation chamber/plunger device to the collection chamber. The user then pushes down the quantitation chamber/plunger device into the collection chamber, thereby transferring a defined 2.5 mL volume of whole blood into the quantitative chamber through the base needle. The user then removes the collection chamber from the quantitation chamber/plunger device. The user then removes the base comprising the needle and replaces it with a base without any needle. The user then places the quantitation chamber/plunger device in a microcentrifuge and applies a force sufficient to separate the plasma from the blood cells. After centrifugation, the user then pushes the plunger device down into the quantitative chamber up to the interface of plasma and blood cell fraction, which enables a defined 1 mL volume of plasma to pass through the plunger filter and into the plunger chamber. The blood cell fraction is retained in the quantitative chamber. The user then detaches the plunger device from the quantitative chamber by unsecuring the quantitate chamber cap. The plunger device comprising the plasma is then further processed or stored until needed.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present invention, which is defined solely by the claims. Accordingly, the present invention is not limited to that precisely as shown and described.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar referents used in the context of describing the present invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

Use of the terms "may" or "can" in reference to an embodiment or aspect of an embodiment also carries with it the alternative meaning of "may not" or "cannot." As such, if the present specification discloses that an embodiment or an aspect of on embodiment may be or can be included as part of the inventive subject matter, then the negative limitation or exclusionary proviso is also explicitly meant, meaning that the an embodiment or an aspect of on embodiment may not be or cannot be included as part of the inventive subject matter. In a similar manner, use of the term "optionally" in reference to an embodiment or aspect of an embodiment means that such embodiment or aspect of the embodiment may be included as part of the inventive subject matter or may not be included as part of the inventive subject matter. Whether such a negative limitation or exclusionary proviso applies will be based on whether the negative limitation or exclusionary proviso is recited in the claimed subject matter.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present invention so claimed are inherently or expressly described and enabled herein.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The invention claimed is:

1. A filtration device for filtering debris from a biofluid sample to generate a filtered biofluid sample, the filtration device comprising:
   a collection container comprising a collection chamber defined by a flexible wall, wherein an entirety of the flexible wall is flexible, a mouth fluidly communicating with the collection chamber and formed through the collection container at a top end, and a filter device defining a bottom of the collection chamber;
   a quantitative container comprising a quantitative chamber in fluid communication with the filter device with the filter device separating the collection chamber from the quantitative chamber, an orifice formed through the quantitative container; and
   a collection chamber cap selectively sealing the mouth of the collection chamber;

wherein, a biofluid sample is capable of being introduced into the collection chamber through the mouth; and wherein, when the collection chamber cap is sealed over the mouth, the flexible wall of the collection container is capable of being squeezed to reduce the volume of the collection chamber and force the biofluid sample through the filter device, the filtered biofluid sample thereafter being contained within the quantitative chamber.

2. The filtration device according to claim 1, wherein the filter device has a pore size of about 0.2 µm to about 50.0 µm.

3. The filtration device according to claim 1, wherein the quantitative chamber has a volume of about 0.5 mL to about 5.0 mL.

4. The filtration device according to claim 1, wherein the quantitative chamber has a volume of 1 mL.

5. A system for processing a biofluid sample, the system comprising a filtration device as defined in claim 1.

6. The filtration device according to claim 1, wherein the quantitative container is a nozzle converging to the orifice.

7. The filtration device according to claim 6, wherein the orifice has a diameter sized so that the filtered biofluid sample drips through the orifice in droplets, each droplet volume ranging between 1 microliter to 200 microliters.

8. The filtration device according to claim 1, wherein a collection device is detachably fitted to the mouth of the collection container, wherein, in use, the collection device receives the biofluid sample and guides the biofluid sample into the mouth to be collected in the collection chamber.

9. The filtration device according to claim 8, wherein the collection device is a funnel with a stem, the stem engaging the mouth when the funnel is attached to the collection container.

10. The filtration device according to claim 1, wherein the collection chamber cap is connected to the collection container through a collection chamber cap living hinge, the collection chamber cap includes a bung for frictionally engaging the mouth.

11. The filtration device according to claim 1, wherein the quantitative chamber further comprises a dispenser cap for selectively sealing the orifice.

12. The filtration device according to claim 11, wherein the dispenser cap is connected to the quantitative container through a dispenser cap living hinge.

13. The filtration device according to claim 11, wherein the dispenser cap seals the filtered biofluid sample within the quantitative chamber when the dispenser cap is connected to the quantitative container.

14. A filtration device for filtering debris from a biofluid sample to generate a filtered biofluid sample, the filtration device comprising:

a collection container comprising a collection chamber defined by a flexible wall, wherein an entirety of the flexible wall is flexible, a mouth fluidly communicating with the collection chamber and formed through the collection container at a top end, and a filter device defining a bottom of the collection chamber;

a quantitative container comprising a quantitative chamber in fluid communication with the filter device with the filter device separating the collection chamber from the quantitative chamber, an orifice formed through the quantitative container, the quantitative container being shaped as a nozzle converging to the orifice;

a collection chamber cap selectively sealing the mouth of the collection chamber; and a collection device detachably fitted to the mouth of the collection container;

wherein, a biofluid sample is capable of being introduced into the collection chamber through the mouth;

wherein, in use, the collection device receives the biofluid sample and guides the biofluid sample into the mouth to be collected in the collection chamber; and wherein, when the collection chamber cap is sealed over the mouth, the flexible wall of the collection container is capable of being squeezed to reduce the volume of the collection chamber and force the biofluid sample through the filter device, the filtered biofluid sample thereafter being contained within the quantitative chamber.

15. The filtration device according to claim 14, wherein the orifice has a diameter sized so that the filtered biofluid sample drips through the orifice in droplets, each droplet volume ranging between 1 microliter to 200 microliters.

16. The filtration device according to claim 14, wherein the collection device is a funnel with a stem, the stem engaging the mouth when the funnel is attached to the collection container.

17. The filtration device according to claim 14, wherein the collection chamber cap is connected to the collection container through a collection chamber cap living hinge, the collection chamber cap includes a bung for frictionally engaging the mouth.

* * * * *